US006605274B1

(12) United States Patent
Dillmann et al.

(10) Patent No.: US 6,605,274 B1
(45) Date of Patent: *Aug. 12, 2003

(54) METHOD FOR IN VIVO REGULATION OF CARDIAC MUSCLE CONTRACTILITY

(75) Inventors: Wolfgang H. Dillmann, Solana Beach, CA (US); Frank Giordano, Del Mar, CA (US); Ruben Mestril, San Diego, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/420,306

(22) Filed: Apr. 11, 1995

(51) Int. Cl.$^7$ ........................ A61K 48/00; C12N 15/861
(52) U.S. Cl. ...................... 424/93.2; 514/44; 435/320.1; 435/455; 435/456
(58) Field of Search ................................ 514/44; 435/6, 435/172.3, 320.1, 325, 455, 456; 935/24, 6, 9, 14, 34, 57, 76; 424/450, 93.2

(56) References Cited

PUBLICATIONS

T. Friedman Sci. Amer. vol–ob Jun. '97 pp. 96–101.*
I. Verma et al. Nature 389:239–42 '97.*
A. Schulick et al. J. Clin. Inv. 99(2) 209–19 '97.*
R. DeMatteo et al. Transplantation 63 (2):315–9 '97.*
K. Chieu Science 260 : 916–7 '93.*
M. Barinaga Science 265 : 738 '94.*
B. Petrof et al. Human Gene Therapy 7: 1813–26 ('96).*
R. Crystal Nature Medicine 1(1) : 15–17 ('95).*
Q. Wang et al. Gene Therapy 2: 775–83 ('95).*
S. Orkin et al NIH Report on Gene Therapy ('95).*
A. Coghlan, New Scientist (Nov. 25, 1995) pp. 14–15.*
D. Brown, Washington Post (Dec. 8, 1995) pp. A1 & A22.*
C. Link, Jr., et al., "Phase I Trial of In Vivo Gene Therapy with the Herpes Simplex Thymidine Kinase/Ganciclovir System for the Treatment of Refractory or Recurrent Ovarian Cancer", pp. 1161–1179; Human Gene Therapy, vol. 7, No. 9, Jun. 10, 1996.
D. Klatzmann, et al., "Gene Therapy for Metastatic Malignant Melanoma: Evaluation of Tolerance to Intratumoral Injection of Cells Producing Recombinant Retroviruses Carrying the Herpes Simplex Virus Type 1 Thymidine Kinase Gene, to be Followed by Ganciclovir Administration", pp. 255–267; Human Gene Therapy, vol. 7, No. 2, Jan. 20, 1996.
J. Deshane, et al., "Transductional Efficacy and Safety of an Intraperitoneally Delivered Adenovirus Encoding an Anti–erbB-2 Intracellular Single–Chain Antibody for Ovarian Cancer Gene Therapy", pp. 378–385, Gynecology Oncology, vol. 64, No. 3, Mar. 1997.
C. H. Evans, et al., "The Promise of a New Clinical Trial—Intra–articular IL–1 Receptor Antagonist", pp. 1–5, Proceedings of the Association of American Physicians, vol. 108, No. 1, 1996.

S. E. Raper, et al., "Safety and Feasibility of Liver–Directed Ex Vivo Gene Therapy for Homozygous Familial Hypercholesterolemia", pp. 116–126, Annals of Surgery, vol. 223, No. 2, Feb. 1996.
T. Tursz, et al., "Phase I Study of a Recombinant Adenovirus–Mediated Gene Transfer in Lung Cancer Patients", pp. 1857–1863, Journal of the National Cancer Institute, vol. 88, No. 24, Dec. 18, 1996.
T. Shimada, "Current Status and Future Prospects of Human Gene Therapy", pp. 176–181, Acta Paediatrica Japonica (1996) 38.
G. Bellon, et al., "Aerosol Administration of a Recombinant Adenovirus Expressing CFTR to Cystic Fibrosis Patients: A Phase I Clinical Trial", pp. 15–25, Human Gene Therapy, vol. 8, No. 1, Jan. 1, 1997.
S. Eck, et al., "Treatment of Advanced CNS Malignancies with the Recombinant Adenovirus H5.010RSVTK: A Phase I Trial", pp. 1465–1482, Human Gene Therapy, vol. 7, No. 12, Aug. 1, 1996.
R. M. Blaese, et al., "T Lymphocyte–Directed Gene Therapy for ADA–SCID: Initial Trial Results after 4 Years", pp. 475–480, Science, vol. 270, Oct. 20, 1995.
W. Waddill, III, et al., "Human Gene Therapy for Melanoma: CT–Guided Interstitial Injection", pp. 63–67, American Journal of Roentgenology, vol. 169, Jul. 1997.
G. McLachlan, et al., "Laboratory and Clinical Studies in Support of Cystic Fibrosis Gene Therapy Using pCMV–CFTR–DOTAP", pp. 1113–1123, Gene Therapy, vol. 3, No. 12, Dec. 1996.
J. Mühlhauser, et al., "Safety and Efficacy of In Vivo Gene Transfer into the Porcine Heart with Replication–Deficient, Recombinant Adenovirus Vectors", pp. 145–153, Gene Therapy, vol. 3, No. 2, Feb. 1996.
X. Xing, et al., "Safety Studies of the Intraperitoneal Injection of E1A–liposome Complex in Mice", pp. 238–243, Gene Therapy, vol. 2, No. 3, Mar. 1997.
D. Stephan, et al., "Gene and other Biological Therapies for Vascular Diseases", pp. 97–110, Fundamental & Clinical Pharmacology, vol. 11, No. 2, 1997.

(List continued on next page.)

Primary Examiner—Scott D. Priebe
(74) Attorney, Agent, or Firm—Foley & Lardner

(57) ABSTRACT

A method for regulating in vivo calcium transport in cardiac muscle of animals suffering from congestive heart failure is disclosed. According to the method, calcium ATPase activity (which decreases as congestive heart failure develops) and cardiac muscle contractility augmented by delivering a gene which operatively encodes the enzyme into the heart. Delivery systems (including recombinant expression vectors) are provided, as are methods for monitoring the expression and effect of the gene product on cardiac performance.

4 Claims, 9 Drawing Sheets

OTHER PUBLICATIONS

F. Giordano, et al., "Intracoronary Gene Transfer of Fibroblast Growth Factor–5 Increases Blood Flow and Contractile Function in an Ischemic Region of the Heart", pp. 534–539, Nature Medicine, vol. 2, No. 5, May 1996.

T. Rothman, et al., "Heart Muscle–Specific Gene Expression Using Replication Defective Recombinant Adenovirus", pp. 919–926, Gene Therapy, vol. 3, No. 10, Oct. 1996.

R. Hajjar, et al., "Physiological Effects of Adenoviral Gene Transfer of Sarcoplasmic Reticulum Calcium ATPase in Isolated Ray Myocytes", pp. 423–429, American Heart Association Circulation, vol. 95, No. 2, Jan. 21, 1997.

R. Wilmott, et al., "Safety of Adenovirus–Mediated Transfer of the Human Cystic Fibrosis Transmembrane Conductance Regulator cDNA to the Lungs of Nonhuman Primates", pp. 301–318, Human Gene Therapy, vol. 7, No. 3, Feb. 10, 1996.

H. Gilgenkrantz, et al., "Transient Expression of Genes Transferred In Vivo into Heart Using First–Generation Adenoviral Vectors: Role of the Immune Response", pp. 1265–1274, Human Gene Therapy, vol. 6, No. 10, Oct. 1995.

M. Aoki, et al., "Efficient In Vivo Gene Transfer into the Heart in the Rat Myocardial Infarction Model Using the HVJ (Hemagglutinating Virus of Japan)—Liposome Method", pp. 949–959, Journal of Molecular and Cellular Cardiology, vol. 29, No. 3, Mar. 1997.

A. Kass–Eisler, et al., "Prospects for Gene Therapy with Direct Injection of Polynucleotides", pp. 232–240, Annals of the New York Academy of Sciences, vol. 772, 1995.

Steven Malosky, et al., "Gene Therapy for Ischemic Heart Disease", pp. 361–368, Current Opinion in Cardiology, vol. 11, 1996.

R.S. Coffin, et al., "Gene Delivery to the Heart In Vivo and to Cardiac Myocytes and Vascular Smooth Muscle Cells In Vitro Using Herpes Virus Vectors", pp. 560–566, Gene Therapy, vol. 3, No. 7, Jul. 1996.

H. B. Nuss, et al., "Reversal of Potassium Channel Deficiency in Cells from Failing Hearts by Adenoviral Gene Transfer: A Prototype for Gene Therapy for Disorders of Cardiac Excitability and Contractility", pp. 900–912, Gene Therapy, vol. 3, No. 10, Oct. 1996.

F. J. Villarreal, et al., "Adenovirus–Mediated Overexpression of Human Transforming Growth Factorβ1 in Rat Cardiac Fibroblasts, Myocytes and Smooth Muscle Cells", pp. 735–742, Journal of Molecular and Cellular Cardiology, vol. 28, No. 4, Apr. 1996.

M. G. Kaplitt, et al., "Long–Term Gene Transfer in Porcine Myocardium after Coronary Infusion of an Adeno–Associated Virus Vector", pp. 1669–1676, The Annals of Thoracic Surgery, vol. 62, No. 6, Dec. 1996.

S. Silvestry, et al., "The In Vivo Quantification of Myocardial Performance in Rabbits: A Model for Evaluation of Cardiac Gene Therapy", pp. 815–823, Journal of Molecular and Cellular Cardiology, vol. 28, No. 5, May 1996.

Lytton, et al., Molecular Cloning of cDNAs from Human Kidney Coding for Two Alternatively Spliced Products of the Cardiac Ca2+–ATPase Gene, *Journal of Biological Chemistry*, vol. 263, No. 29, pp. 15024–15031 (1988).

Zarian–Herzberg, et al., "Characterization of Rabbit Cardiac Sarco(endo)plasmic Reticulum Ca2+–ATPase Gene," *Journal of Biological Chemistry*, vol. 265, No. 8, pp. 4670–4677 (1990).

Dhalla, et al., "Pathophysiology of cardiac dysfunction in congestive heart failure," *Canadian J. Cardiology*, 9:873–887 (1993).

Guzman, et al., "Efficient Gene Transfer Into Myocardium by Direct Injuection of Adenovirus Vectors", *Circulation Research*, vol. 73, No. 6, Dec. 1993.

Seachrist, "Gene Transfer to Spark a Failing Heart", *Science*, 264:507–508 (1994).

Milano, et al., "Enhanced Myocardial Function in Transgenic Mice Overexpressing the $\beta_2$–Adrenergic Receptor", *Science*, 264:582–586 (1994).

Brody, et al., "Adenovirus–Mediated in Vivo Gene Transfer", *Annals NY Acad. Sci.*, 716:90–101 (1994).

* cited by examiner

```
                    =-3500 TTCGAGGTGGTTAGCCGGGAGAAGGTGACTCAGCTCACAATGGGCTGCTTTAATGATTGGAGCTG TCCAA
                           ATATGGAGCAGGCTGCCTCCTGTGGCCCCCACCACTTCCCGGGAGGCCTGCAGAGGGCTGAGACCAGGCC
                    =-3360 CGGCCTCTTTTGCAAGTCACCTCCTGGCTTTTCTG TCTGAATAGCTTTTTAAACT AACCTGCTTTTTTTC  ← MEF-2
                           CCCGGTTAGGTAAGGTCCTCCTTTATTCGTGCCTCTGAAGGTCTTTCATCTTTCTGCATTGCACGCTGCG
        M-CAT →     =-3220 TCTTTCCGTCT CCTTCCTG TCCTCAAGTGATTAAGTATGTGGTTCTGAGCCTTGTTGGAAGACGGTAACC
        MEF-2 →            TTT CTTATTAAAG CCTTGCAAACCAGCGGAGTACAGCATTGCACACAAAACAAACTGAGCCCCATTTTTT
        MEF-2 →     =-3080 TTTTT TTTTTTTTAA GGCAGGTTCTCACTAAGCTGGCCTGGAATTCACTATGTAGATCACCTTAGTCTAC
                           ACCTCATCCTCAGCTGCCTCTGCCTCCTGAGCGTTGGGATTATAGGTGCCGTGACTACGCGCCAGTTTCT
                    =-2940 CCTTCTTTTTGAAGCGAGATGACCCTTTTATGTGTTTCTCCCAACT TTATTTCTA CA TAAAAGTAG CCAG  ← MEF-2(2)
                           GGATTCTGCCTCCAGGAGTCTGGGTTCAAGATCAGTTTTGCCAACTCCTGAGTCAGAGGGCTCAGAGATA
                    =-2800 ACGACAGGCTGAGGAGACAAAGACCTAGTTGGCATGAT CATATG CCTGGGGCCAATGCTGAGCTAAAAAT  ← E-Box
        M-CAT →            CATACTATTAGTTTAAGGGAG CATTCCA ACCTTCAGTAAAAAAGAAACACCTTGCAAAGAA CATTCCA GA  ← M-CAT
        E-Box →     =-2660 AGGG TAATTG GAAGATGGTAGCGGTACCTATGAGACTAAGGGCGTCATTTCTGGGAGCCCCATAGGCAGC
                           TTTGTTTTAATACTAAGCCTCACAGAATCTCATAGGCCAGTGGTCCGGGGGCCAAAATAAATCCAGTT TA
        M-CAT →            TTCCT GAATGGCCC  GAP ≈ 300 bp TTTGTGCTGCACAGCCCCTTTGCAGNNNCTGATGGGTTGAG
                           GAGGGTGGACTCTCATTCACTGAAACCGTACCTACTCAATAAATGCGCAGATGCTGGGGCTAGGCCTTGT
                    -2117  ACTGAGTGTGGACAAGACAAGCTCTGTTCGCGTGGACCTCAAATCTGGATGTCGTACAAGACGCTAGGAG
                           GCCGGCAGTGAGCAGCTAAACGAAATGTACAGCCCGTTTTCCATAGATAAGTGTTAGGGAGGAGANNCCG
                    -1977  CTTCTTCGGAGATAGCGGGGCATACTGGGGAGGGGAGCGGCTTTAGATAATAAAAGCATCTTTCCGGAGG
                           GACATATAGATTCGGAAGATGGCCGGG GCGGGCGCG CCG CCGGGGCCG GG GCCGGGCCG CCG CCGCCCC  ← Egr-1(7)
                    -1837  GGGAGAAGAACCAGGAACTCATGTTGTAAGGTGCACCTACAGCCTCTGAAAGAGGGGCTACACAAAACA
                           AAGAAACGAACAAAAAATGAAACCCAATGAAACCCAGTGAGCATCTCAAACAGAG AGGTCATGACCTTCC  ←M-CAT/Egr-1
                    -1697  TGCTCTCAGCGCCTCTTGCAGTTGGTGTGAAAAACACGAAGGCAGGCAGAACTGGAATCAAGGAGGAGGA
                           AGACCCACGGGCTCTCCGTCACCGCACCCCCACCTCGCAGGCCGTCACCTGATCCTCCAGAAGAGGCTGT
                    -1557  GACCTAACCAAGTTTCCACCTTGCTTCTAGGCAGTGCATTGCTATACAGTAGAATTTTTGTTTGTTTGTT
                           TCGTGTAGGGTTCTGTTGGTCCTATTCCAAGTATCAATCAGAACTGCATGCCAGCCACCACTCCTTGTCC
        CREB →      -1417  ATAATTAAA TGACGTAC TTGATTTTTTTTTTCAGTCGGGTAAAGCACCGTGATTTCGATCTGCTGAAGG
                           TATCTATCTTAAGTCTTGAGCGGACCCTTGTTGGAACGGACTTAAGTGTTGGGGGGGGAGCGCTTGCTAA
        MEF-2 →     -1277  ACACTCAAGTAGACGAAATGCT TTATTTTGCA ATCTATTTCCTTGCTGGAGCCGCTTTTTGTGAAGATAT
                           TCGTGAATTCAATGCAAAGGTCCTCCTCCCTGTTAAGTATGGCTTCCCACTTCTCTGCC TTAAAAAAAA T  ← MEF-2
                    -1137  TTTTTTTGATGTTTTAGACAAGGACCAATATCGAAGGCTGGTTCTAAACT CAAGTGTC TGGACGTGACCT  ← E-Box
                           TGAACTCTTGAGTCGTCGCTTCCACCTCTGGTGCTGGGATCACAGGCGGGCACACACTTTAACTCCGTGT
                    -997   GCGCTCATTATATTGGAAAAAATTACGTTCCATGCTAGGCTCTCTACAGACCTCACCGACACAACAA CAT  ← E-Box
        MEF-2 →            ATG TGGT TTAAGAATAG ATTTGGGATTCAAGGCTCCTTTTCTCCATTGGGGGAAGTGAAAGTCTATATAC
                    -857   TAGCCTTCATTTTTGAAGCCAAACGCAAGCTACCTAGCACAGGCGTAGCTGTTACAGCATAACCTGTGAC
                           TTCTATGCAGACGTGTGTCAAAGGCTGTGTGAGCTACTAAAACCGAAATAAAACTTCCT CCTTCCT CCCC  ← M-CAT
                    -717   CAAGAGTGGGATTCTGTCGGGGCACAGAACCGCAGGGGAAGGAAGGGCTGGTGTTGGCGTGCGATGGACA
       C₂TRANS →           TGGGGCTTTC GGCTGGGG GTGTGGGATCCGGTGTCCCGACGCGA CAGATG AGCGCTTTTGGCTGTGAGGG  ← E-Box
        M-CAT →     -577   AAGGGAACTGCG GAATTCC TCCCCTTGGTTGCTGAGGGGGCTCTGAAGGAGACATTAGGATGCAGAGCA
        TRE-1 →            CGGCTCGCGCTGCCCAGGGCGCGG AGGCAAGCCAAGGACA CCAGTCCCTGCGCGCCTCGGTCCCCAGCGT
                    -437   TCCGGCGCCTCCCTGCCACCACGCGGCCCCAGGAAGTCCCCCCTCAGCGGCGGGGCCCCAGCACAGAGC
       C₂TRANS →           G CCCACCCG TGAGCTCCGCGATC TATTCCT GCACGCGGACGGAATGGGAAAGCCG CGACCGCGTAAGGTC  ← TRE-2
        M-CAT→
           Sp1 →    -297   G GGCTCGCCCGCCGC CCGCCC GGCCGCAGCGAGCACAGCGAG    GACGCGGAGGTGGCCTGCGCGC
          TRE3 →            GCACACGCGCG CGGCCTCGATCCGGGTTA CTGG GGGCGG CGCGCGGGAGGAGGCGGGGCCTGCCGGCAGC  ← Sp1
                    -157   GTGGGCGCGCACGCGCCGCGGGAGGGCGCCGGGGGAGGGGCGGGGCCGCG CCGCCC GCGCCGCGCTGGG  ← Sp1
        E-Box →            CTCTCTCGGCCAATGAGCGGCGTC CACATG CCCGGCGGCGGCGAGAGGGGAGGCAGCGGCGGATAAATGC
                    -17    TATTAGAGCAGCCTCCG
```

FIG. 1

SEQUENCE LISTING

<160> NUMBER OF SEQ ID NOS: 1

<210> SEQ ID NO 1
<211> LENGTH: 3517
<212> TYPE: DNA
<213> ORGANISM: Rattus sp.
<220> FEATURE:
<221> NAME/KEY: modified_base
<222> LOCATION: (995)..(1294)
<223> OTHER INFORMATION: a, t, c, g, other or unknown
<220> FEATURE:
<221> NAME/KEY: modified_base
<222> LOCATION: (1320)..(1322)
<223> OTHER INFORMATION: a, t, c, g, other or unknown
<220> FEATURE:
<221> NAME/KEY: modified_base
<222> LOCATION: (1541)..(1542)
<223> OTHER INFORMATION: a, t, c, g, other or unknown

<400> SEQUENCE: 1

```
ttcgaggtgg ttagccggga gaaggtgact cagctcacaa tgggctgctt taatgattgg      60
agctgtccaa atatggagca ggctgcctcc tgtggccccc accacttccc gggaggcctg     120
cagagggctg agaccaggcc cggcctcttt tgcaagtcac ctcctggctt ttctgtctga     180
atagcttttt aaactaacct gcttttttc cccggttagg taaggtcctc ctttattcgt     240
gcctctgaag gtctttcatc tttctgcatt gcacgctgcg tctttccgtc tccttcctgt     300
cctcaagtga ttaagtatgt ggttctgagc cttgttggaa gacggtaacc tttcttatta     360
aagccttgca aaccagcgga gtacagcatt gcacacaaaa caaactgagc cccatttttt     420
tttttttttt tttaaggcag gttctcacta agctggcctg gaattcacta tgtagatcac     480
cttagtctac acctcatcct cagctgcctc tgcctcctga gcgttgggat tataggtgcc     540
gtgactacgc gccagtttct ccttcttttt gaagcgagat gaccctttta tgtgtttctc     600
ccaactttat ttctacataa aagtagccag ggattctgcc tccaggagtc tgggttcaag     660
atcagttttg ccaactcctg agtcagaggg ctcagagata cgacaggct gaggagacaa     720
agacctagtt ggcatgatca tatgcctggg gccaatgctg agctaaaaat catactatta     780
gtttaaggga gcattccaac cttcagtaaa aagaaacac cttgcaaaga acattccaga     840
agggtaattg gaagatggta gcggtaccta tgagactaag ggcgtcattt ctgggagccc     900
cataggcagc tttgttttaa tactaagcct cacagaatct cataggccag tggtccgggg     960
gccaaaataa atccagtttta ttcctgaatg gcccnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnntttgtg ctgcacagcc cctttgcagn    1320
nnctgatggg ttgaggaggg tggactctca ttcactgaaa ccgtacctac tcaataaatg    1380
cgcagatgct ggggctaggc cttgtactga gtgtggacaa gacaagctct gttcgcgtgg    1440
acctcaaatc tggatgtcgt acaagacgct aggaggccgg cagtgagcag ctaaacgaaa    1500
tgtacagccc gttttccata gataagtgtt agggaggaga nnccgcttct tcggagatag    1560
cggggcatac tggggagggg agcggcttta gataataaaa gcatctttcc ggagggacat    1620
atagattcgg aagatggccg gggcgggcgc gccgccgggg ccggggccgg gccgccgccg    1680
```

-continued

```
ccccgggag aagaaccagg aactcatgtt gtaaggtgca cctacagcct ctgaaagagg    1740
gggctacaca aaacaaagaa acgaacaaaa aatgaaaccc aatgaaaccc agtgagcatc    1800
tcaaacagag aggtcatgac cttcctgctc tcagcgcctc ttgcagttgg tgtgaaaaac    1860
acgaaggcag gcagaactgg aatcaaggag gaggaagacc cacgggctct ccgtcaccgc    1920
accccccacct cgcaggccgt cacctgatcc tccagaagag gctgtgacct aaccaagttt    1980
ccaccttgct tctaggcagt gcattgctat acagtagaat ttttgtttgt ttgtttcgtg    2040
tagggttctg ttggtcctat tccaagtatc aatcagaact gcatgccagc caccactcct    2100
tgtccataat taaatgacgt acttgatttt ttttttttcag tcgggtaaag caccgtgatt    2160
tcgatctgct gaaggtatct atcttaagtc ttgagcggac ccttgttgga acggacttaa    2220
gtgttggggg gggagcgctt gctaaacact caagtagacg aaatgcttta ttttgcaatc    2280
tatttccttg ctggagccgc tttttgtgaa gatattcgtg aattcaatgc aaaggtcctc    2340
ctccctgtta agtatggctt cccacttctc tgccttaaaa aaaatttttt ttgatgtttt    2400
agacaaggac caatatcgaa ggctggttct aaactcaagt gtctggacgt gaccttgaac    2460
tcttgagtcg tcgcttccac ctctggtgct gggatcacag gcgggcacac actttaactc    2520
cgtgtgcgct cattatattg gaaaaaatta cgttccatgc taggctctct acagacctca    2580
ccgacacaac aacatatgtg gtttaagaat agatttggga ttcaaggctc cttttctcca    2640
ttgggggaag tgaaagtcta tatactagcc ttcattttg aagccaaacg caagctacct    2700
agcacaggcg tagctgttac agcataacct gtgacttcta tgcagacgtg tgtcaaaggc    2760
tgtgtgagct actaaaaccg aaataaaact tcctccttcc tcccccaaga gtgggattct    2820
gtcgggcac agaaccgcag gggaaggaag ggctggtgtt ggcgtgcgat ggacatgggg    2880
ctttcggctg ggggtgtggg atccggtgtc ccgacgcgac agatgagcgc ttttggctgt    2940
gagggaaggg aactgcggaa ttcctcccct tggttgctga ggggggctct gaaggagaca    3000
ttaggatgca gagcacggct cgcgctgccc agggcgcgga ggcaagccaa ggacaccagt    3060
ccctgcgcgc ctcggtcccc agcgttccgg cgcctccctg ccaccacgcg gccccaggaa    3120
gtcccccctc agcggcgggg ccccccagcac agagcgccca cccgtgagct ccgcgatcta    3180
ttcctgcacg cggacggaat gggaaagccg cgaccgcgta aggtcgggct cgcccgccgc    3240
ccgcccgggc cgcagcgagc acagcgagga cgcggaggtg gcctgcgcgc gcacacgcgc    3300
gcggcctcga tccgggttac tgggggcggc gcgcgggagg aggcggggcc tgccggcagc    3360
gtgggcgcgc acgcgccgcg ggagggcgcc ggggagggg gcgggccgc gccgcccgcg    3420
ccgcgctggg ctctctcggc caatgagcgg cgtccacatg cccggcggcg gcgagagggg    3480
aggcagcggc ggataaatgc tattagagca gcctccg                             3517
```

METHOD FOR IN VIVO REGULATION OF CARDIAC MUSCLE CONTRACTILITY

This invention was made with Government support under Grant No. HL25022 awarded by the National Institute of Health. The Government has certain rights in this invention.

BACKGROUND OF THE INVENTION

1. Field of the Invention

The invention relates to methods for regulating cardiac muscle contractility. More specifically, the invention relates to methods to increase in vivo levels of cardiac sarcoplasmic reticulum (SR) calcium$^{2++}$ ATPase (SERCA2) by in vivo delivery of a gene which operatively encodes SERCA2 protein.

2. History of the Prior Art

Congestive heart failure is one of the leading causes of death among adults in the United States. As compared to cardiac ischemia (an acute event resulting from obstruction or loss of blood supply to the heart), congestive heart failure is a relatively insidious event associated with the gradual loss of cardiac muscle contractility and adaptability of the heart to stress. Ultimately, absent effective treatment, the CHF heart loses its ability to pump blood at a rate sufficient to meet the metabolic requirements of the body.

Although the abnormalities in cardiac function which accompany congestive heart failure (CHF) vary, decreased release from the SR of the calcium$^{2++}$ ions required for activation of contractile proteins is a common characteristic of the CHF syndrome. The significance of this loss can be best understood in the context of the role that calcium transport plays in the normal functioning of the heart.

Briefly, the SR is a membranous structure which surrounds each myofibril of cardiac muscle. SERCA2 is contained within the SR membranes and serves to actively transport 70 to 80% of free calcium ions into the SR intracellular space during diastolic relaxation of cardiac muscle. Much of the remaining calcium ions available for transport are removed from the cytoplasm by a SR sodium/calcium transport exchange system as well as, to a far lesser extent, transport driven by ATP hydrolysis CATALYZED by sarcolemma calcium ion ATPase and through mitochondrial calcium uptake (Bassani, et al., *J. Physiol.* 453:591–608, 1992 and Carafoli, E., *Ann. Rev. Biochem.,* 56:395–433, 1987).

Given that both the ATP hydrolytic activity of SERCA2 and absolute levels of SERCA2 mRNA are decreased in the CHF heart (Hasenfuss, et al., *Circ. Res.,* 75:434–442, 1994 and Studer, et al., *Circ. Res.* 75:443–453, 1994), it has been widely postulated that the impairment of the CHF heart's ability to receive blood at low pressures is directly linked to delays in SERCA2 mediated transport of contraction-activating calcium ions into the SR, which in turn results in a slowing of diastolic relaxation of the heart (see, e.g., Grossman, W., *N. Engl. J. Med,* 325:1557–1564, 1991; Lorell, B H, *Ann. Rev. Med,* 42:411–436, 1991; and, Arai, et al., *Circ. Res.,* 74:555–564, 1994). These observations, particularly with respect to reductions in levels of mRNA's coding for SERCA2 have been confirmed in humans as well as other mammalian species (see, re human SERCA2 mRNA levels, Arai, et al., supra and Mercadier, et al., *J. Clin. Invest.,* 85:305–309, 1990; also, re lowering of SERCA2 mRNA levels in hypertrophied heart tissue of other mammalian species, see, e.g., Wang, et al., *Am. J. Physiol.,* 267:H918–H924, 1994 [ferrets]; Afzal and Dhella, *Am. J. Physiol.,* 262:H868–H874, 1992 [rodents]; and, Feldman, et al., *Circ. Res.,* 73:184–192, 1993 [rodents]).

Despite the interest in recent years regarding the role of calcium transport in CHF, the molecular basis for the impairment of SERCA2 calcium transport activity is poorly understood and has not yet been exploited in a regime for the treatment of CHF. Instead, current therapeutic modalities for CHF syndrome are largely non-specific in the sense that are not directly targeted toward the biochemical and molecular events which are believed to accompany, if not cause, the abnormalities of function which lead to failure of the CHF heart. For example, pharmaceutical treatment of CHF by administering adrenaline-like drugs stimulates cardiac muscle contraction but does not correct the underlying condition which caused the diminishment in the contractility of the muscle.

Thus, replacement and/or increase of in vivo levels of cardiac proteins is an intriguing alternative for the treatment and control of the progression of CHF in humans. However, achieving this goal by introducing cardiac proteins or peptides into heart tissue is unlikely to be successful. Of primary concern is the risk of potential toxicities, particularly at dosages sufficient to produce a biological response to the protein. From a practical perspective, there is also the problem of the cost associated with isolating and purifying or synthesizing the proteins. Moreover, the clinical impact of the proteins would also be limited by their relatively short half-life in vivo due to degradation by any proteases present in the target tissue.

For these reasons, introduction of a protein into a patient by delivery of a gene which will express the protein is an intriguing alternative to administering the protein itself. To that end, a variety of strategies have been developed for the introduction of exogenous genes into target cells. Most gene therapy protocols proposed to date for use in humans have focused on ex vivo gene transfer; e.g., by retroviral transfection of cells for implantation into target tissue (see, e.g., Anderson, W F, *Science,* 256:808–813, 1992 and Miller, A D, *Nature,* 357:455–460, 1992 [treatment of adenosine deaminase deficiency]). However, the usefulness of such protocols has proved to be limited by their relative inefficiency of protein expression as well as the limited accessibility of target organs and tissues.

In vivo gene delivery methods are therefore a topic of great interest in the art. To that end, several systems have been developed to achieve this goal, including introduction of "naked" polynucleotides (plasmids), plasmids linked to viruses, plasmids cointernalized with viruses, as well as encapsulation and delivery of gene constructs within liposomes.

For example, work at the NIH was reported in 1984 which showed that intrahepatic injection of naked, cloned plasmid DNA for squirrel hepatitis into squirrels produced both viral infection and the formation of antiviral antibodies in the squirrels (Seeger, et al., *Proc. Nat'l. Acad. Sci USA,* 81:5849–5852, 1984). Several years later, Felgner, et al., reported that they obtained expression of protein from "naked" polynucleotides (i.e., DNA or RNA not associated with liposomes or a viral expression vector) injected into skeletal muscle tissue (Felgner, et al., *Science,* 247:1465, 1990; see also, PCT application WO 90/11092). Felgner, et al. surmised that muscle cells efficiently take up and express polynucleotides because of the unique structure of muscle tissue, which is comprised of multinucleated cells, sarcoplasmic reticulum and a transverse tubular system which extends deep into the muscle cell.

Similar systems for delivery genes directly into target tissue have been reported by Stribling, et al., *Proc. Natl. Acad. Sci. USA*, 89:11277–11281, 1992 (protein expression detected after aerosol delivery of a liposome encapsulated gene); and, Tang, et al., *Nature*, 356:152–154, 1992 (injection with a vaccine "gun" of an hGH plasmid coupled to colloidal gold beads into the skin of mice resulted in hGH protein expression without eliciting an immune response to the injected gene). Although generally effective for producing high levels of protein expression within muscle cells, direct injection of DNA or RNA into muscle tissue for long-term therapy requires use of repeated injections to offset loss of expression from gene degradation. This approach may not only be time-consuming and expensive, but may also be impractical for long-term therapy due to inflammation caused at and near the site of injection. Thus, although useful in short-term or emergency therapies, less invasive means for introduction of expressible genes into target tissue will generally be preferred over direct injection into the target tissue.

Further, most methods for in vivo gene delivery free of a recombinant expression vector suffer from inefficient target cell transfection and relatively low protein expression. Thus, recombinant expression vectors (especially non-replicable vectors) presently remain the preferred vehicle for in vivo gene delivery.

Cardiac myocytes have been shown to be suitable targets for in vivo gene delivery. For example, one recent proposal for treatment of CHF would replace and/or enhance the numbers of active $\beta_2$-adrenergic receptors in myocytes of the CHF heart. Studies in mice have indicated that use of direct transplantation techniques to introduce genes which encode such receptors leads to increased in vivo contractility of the heart muscle even in the absence of an exogenous adrenaline source (Lefkowitz, et al., *Science*, 264:582–586, 1994). Adenovirus vectors in particular have been shown to be successful vehicles for delivery of genes to cardiac myocytes (see, e.g., Guzman, et al., *Circ. Res.*, 73:1202–1207, 1993 and Muhlhauser, et al., *Circulation*, 88(Part 2):1–475, 1993).

SUMMARY OF THE INVENTION

The details of the preferred embodiment of the present invention are set forth in the accompanying drawings and the description below. Once the details of the invention are known, numerous additional innovations and changes will become obvious to one skilled in the art.

The invention is a method for augmenting calcium transport into the SR of heart muscle by elevating in vivo expression of catalytically active SERCA2 by introducing a polynucleotide which operatively encodes SERCA2 into such tissue. In an embodiment preferred for its efficiency of target cell transfection, the SERCA2 encoding polynucleotide is delivered into heart tissue via a non-replicable viral recombinant expression vector, most preferably an adenovirus construct. Alternatively, the SERCA2 encoding gene may be provided by encapsulation in liposomes or by administration of "naked" nucleotides. Delivery of the SERCA2 gene may be made surgically (i.e., by direct introduction of the vector or transfected cells into target tissue) or by intracoronary infusion.

The enhancement in transport of calcium ions to the SR provided by increased SERCA2 activity in the SR will moderate activation of myofibril contractions in the heart. Thus, a particular advantage of the method of the invention is the assistance it will provide the heart in adjusting to the abnormalities associated with CHF, especially by shortening the early phase of diastolic relaxation of heart muscle.

One use for the method of the invention is for short-term amelioration of CHF in patients who are awaiting interventional therapy (e.g., transplantation) and/or who are already undergoing treatment for CHF. Use of the method of the invention is also expected to benefit patients who are at risk for, and have begun to suffer from, the abnormalities in heart function associated with CHF.

In another aspect of the invention, transgenic animals are provided for use in developing vectors for use in, and testing the application of, the method of the invention. Methods for monitoring the efficacy of the method of the invention as used for treatment of CHF are also described.

BRIEF DESCRIPTION OF THE DRAWINGS

FIG. 1 is a partial nucleotide sequence for the regulatory region of the SERCA2 rat genomic clone (SEQ ID NO1). Nuclear response elements are indicated by boxes with arrows labeled with common designations; to wit: M-CAT (muscle specific transcription factor; Mar and Ordahl, *Mol. Cell. Biol.*, 14:4271–4285, 1990), TRE's (thyroid response elements 1–3), Egr-1 (Huang, et al., *Biochem. Biophys. Res. Comm.*, 200:1271–1276,1994), MEF-2 (Nakatjusi, et al., *Mol. Cell. Biol.*, 12:4384–4390, 1992), CREB binding site (Gonzalez, et al., Mol. CellBiol., 11:1306–1312, 1991), Sp1 (Mitchell and Tijan, *Science*, 245:371–378, 1989) and the common E box motif (Olsen, *Genes & Dev.*, 4:1454–1461, 1990). The SERCA2 regulatory region includes 3.5 kb upstream from the initiation codon.

FIG. 1 is a map of a SERCA2 encoding plasmid under the control of the tetracycline operator system.

Figure 2:
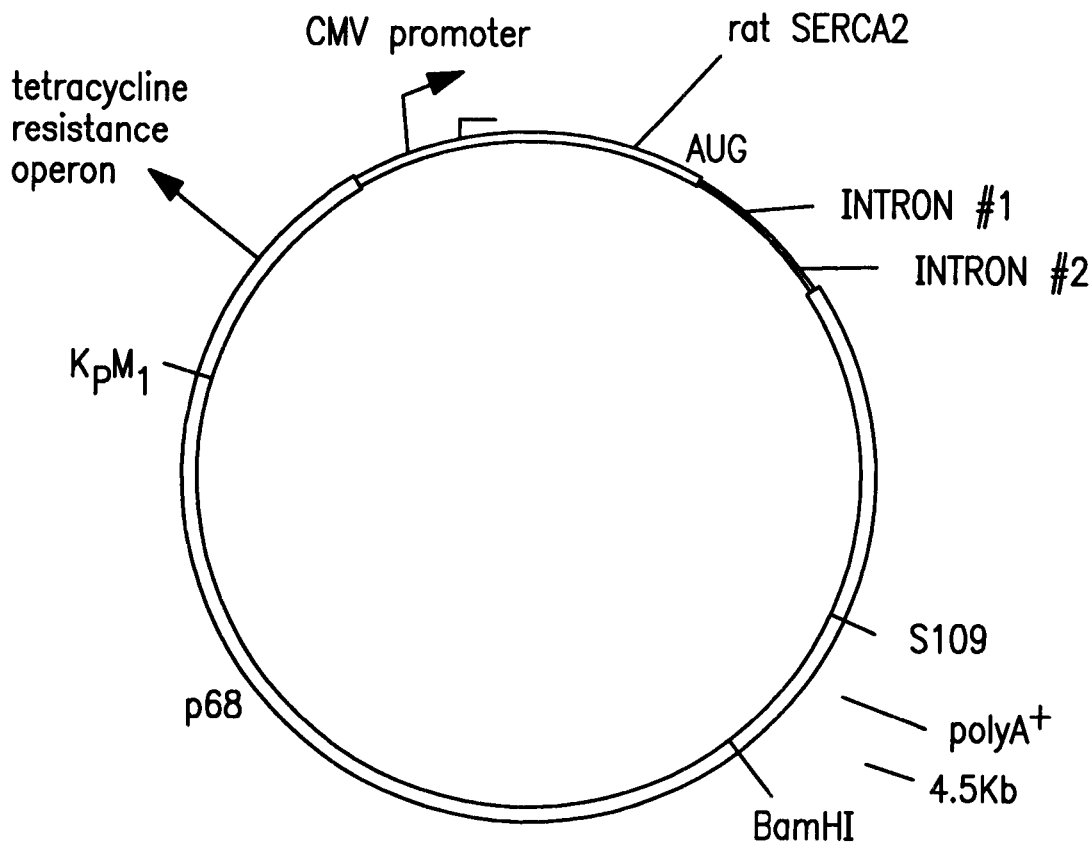
FIG. 2 is a map of a SERCA2 encoding plasmid under the control of the tetracycline operator system.

(average values are represented by Cell #27) and in unfransfected neonatal myocytes (average values are represented by Cell #42). Calcium transients are measured fluorimetrically and expressed as a function of time (x axis).

DETAILED DESCRIPTION OF THE INVENTION

Throughout this description, the preferred embodiment and examples shown should be considered as exemplars, rather than as limitations on the present invention.

A. DEFINITIONS

The following definitions are provided to simplify discussion of the invention. Those skilled in the art will, however, recognize that these definitions may be expanded to include equivalents without departing from the legitimate scope or spirit of the invention. For this reason, these definitions should not be construed as limiting the invention.

1. "SERCA2 polynucleotide" refers to DNA or RNA and can include sense and antisense strands as appropriate to the goals of the therapy practiced according to the invention. As used herein, "polynucleotide" refers to a polymer of deoxyribonucleotides or ribonucleotides, in the form of a separate fragment or as a component of a larger construct. A polynucleotide sequence can be deduced from the genetic code, however, the degeneracy of the code must be taken into account. Polynucleotides of the invention include sequences which are degenerate as a result of the genetic code, which sequences may be readily determined by those of ordinary skill in the art.
2. "Operatively encoding" refers to a polynucleotide which has been modified to include promoter and other sequences necessary for expression and, where desired, secretion of the desired translation product; e.g., a peptide or protein. All the embodiments of the invention can be practiced using known recombinant expression vectors. Preferably, these vectors will include cDNA('s) which encode for the desired translation product. Therefore, unless context otherwise requires, it will be assumed that "polynucleotide" refers to operatively encoding sequences contained in a suitable recombinant expression vector, examples of which are provided herein.
3. "Synthesis" refers to well-known means of synthesizing polynucleotide and polypeptide sequences and may include isolation and purification of native polynucleotides and proteins.
4. "Peptide" refers to small peptides, polypeptides, oligopeptides and proteins which have a desired biological effect in vivo.
5. "Delivery" refers to known means of introducing operatively encoding polynucleotides to a host. Those of ordinary skill in the art will be familiar with, or can readily identify, such delivery means; however, reference with respect to particularly useful means for delivery may be made to "Novel Drug Delivery Systems", (Marcel Dekker, 1992), the relevant disclosures of which are incorporated herein by this reference for the purpose of illustrating the state of knowledge in the art concerning techniques for drug delivery.
6. "Host" refers to the recipient of the therapy to be practiced according to the invention. The host may be any vertebrate, but will preferably be a mammal. If a mammal, the host will preferably be a human, but may also be a domestic livestock or pet animal.
7. "Target tissue" refers to the tissue of the host in which expression of the operatively encoding polynucleotide is sought.
8. "Antibody" refers to whole immunoglobulin of any class, chimeric antibodies, hybrid antibodies with dual or multiple antigen specificities and fragments including hybrid fragments. Also included within the meaning of "antibody" are conjugates of such fragments, and so-called antigen binding proteins (single chain antibodies) as described, for example, in U.S. Pat. No. 4,704,692, and anti-idiotypic antibodies (antibodies that bind other antibodies) as described, for example, in U.S. Pat. No. 4,699,880.
9. "Recombinant expression vector" refers to systems of polynucleotide(s) which operatively encode polypeptides expressible in eukaryotes or prokaryotes. Methods of expressing DNA sequences having eukaryotic or viral sequences in prokaryotes are well known in the art. Biologically functional viral and plasmid DNA vectors capable of expression and replication in a host are also well known in the art. Hosts can include microbial, yeast, insect and mammalian organisms.

B. POLYNUCLEOTIDE CONSTRUCTS FOR USE IN THE METHOD OF THE INVENTION

The partial nucleotide sequence for a genomic clone of rat SERCA2 is shown in FIG. 1 (see also, Rohrer, et al., *J. Biol. Chem.,* 263;6941–6944, 1988 [rat SERCA2 mRNA], the reported sequence from which is incorporated herein for purposes of reference). The clone was obtained by conventional hybridization techniques as described in Rohrer, et al., *J. Biol. Chem.,* 266:8638–8646, 1991 (the disclosure of which is incorporated herein for purposes of reference), which also sets forth the initiation and stop codons for transcription of the clone (see, FIG. 1 and Example 1).

The nucleotide sequence of the SERCA2 isoform of calcium ATPase (i.e., the "slow" isoform of skeletal muscle as compared to the "fast" isoform of striated muscle) is 90%+ conserved among mammalian species. SERCA2 has therefore been fairly readily identified and sequenced from skeletal muscle tissue in non-rodent mammalian species, including humans (GENBANK #J4025; see also, GENBANK M23114–23116, M23277–23279, and Lytton and MacLennan, *J. Biol. Chem.,* 263:15024–15031, 1988); and rabbits (MacLennan, D H, *Nature,* 316:697–700, 1985, and GENBANK M33834). Although those of ordinary skill in the art will recognize that use of the human SERCA2 polynucleotide would be greatly preferred in human therapies, the rat SERCA2 polynucleotide was simpler to use and preferred for purposes of the experiments described in the Examples.

It will also be appreciated by those of skill in the art that the method of the invention, which is described herein specifically with reference to SERCA2, may be advantageously adapted to use for delivery of other cardiac proteins whose expression and activity are impaired in the CHF heart. In particular, the gene encoding the mammalian calcium/sodium exchanger is a particularly attractive subject for delivery to the heart according to the method of the invention in the same manner as is described herein for delivery of SERCA2 polynucleotide.

To obtain and use of the SERCA2 sequences included in this disclosure and those known in the art, DNA and RNA may also be synthesized using automated nucleic acid synthesis equipment well known in the art. Use of the well-known polymerase chain reaction (PCR) is particularly preferred for generating mixtures of polynucleotides. Genomic nucleic acids may be prepared by means well-known in the art such as the protocols described in Ausubel, et al., *Current Protocols in Molecular Biology*, Chs. 2 and 4 (Wiley Interscience, 1989). cDNA can be synthesized according to means well known in the art (see, e.g., Maniatis, et al., *Molecular Cloning; A Laboratory Manual* (Cold Spring Harbor Lab, New York, 1982). A cDNA expression library containing polynucleotides of interest can also be screened by means well known in the art.

For example, these means include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). The development of specific DNA sequences encoding or fragments thereof, can also be obtained by: 1) isolation of double-stranded DNA sequences from the genomic DNA: 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture.

A cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of therapeutic and/or immunogenic peptides having at least one epitope using antibodies specific for the peptides. Such antibodies can be either polyclonally or monoclonally derived and used to detect expression product indicative of the presence of cDNA of interest.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The SERCA2 polynucleotide to be used in the invention may be DNA or RNA, but will preferably be a complementary DNA (cDNA) sequence. The polynucleotide sequences used in the invention must be (a) expressible and (b) either non-replicating or engineered by means well known in the art so as not to replicate into the host genome. Preferably, a polynucleotide which operatively encodes a SERCA2 protein will be used in the invention as part of a recombinant expression vector, most preferably an adenovirus construct.

Illustrations of the preparation of polynucleotides suitable for use in the invention follow and specific examples showing how particular polynucleotide compositions were made are provided infra. It will, however, be apparent to those skilled in the art that other known means of preparing nonreplicating polynucleotides may also be suitable.

Polynucleotides of the invention include functional derivatives of known polynucleotides which operatively encode for SERCA2 protein. By "functional derivative" is meant a polynucleotide which will encode "fragments," "variants," "analogs," or "chemical derivatives" of SERCA2. A "fragment" of a molecule includes any peptide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties which are known in the art to be capable of mediating such effects are disclosed, for example, in *Remington's Pharmaceutical Sciences*, 16th Ed., Mack Publishing Co., Easton, Pa. (1980).

The SERCA2 polynucleotides may be conjugated to or used in association with other polynucleotides which operatively code for regulatory proteins that control the expression of these polypeptides or may contain recognition, promoter and secretion sequences. Those of ordinary skill in the art will be able to select regulatory polynucleotides and incorporate them into SERCA2 polynucleotides of the invention without undue experimentation. For example, suitable promoters for use in murine or human systems and their use are described in *Current Protocols in Molecular Biology*, supra at Ch. 1.

A particularly preferred form of a SERCA2 polynucleotide for use in the invention will be one which has been incorporated into a recombinant expression vector. Use of an recombinant expression vector will prolong expression of the gene in target tissue.

Suitable recombinant expression vectors are well-known in the art and include the vectors described in *Current Protocols in Molecular Biology*, supra at Ch. 1. Two particularly preferred plasmid promoter vectors are the pRSV (Rous sarcoma virus) and pCMV (cytomegalovirus) promoter vectors, particularly the latter. This preference is based on observations that higher levels of expression are achieved in this context when the CMV promoter is employed.

A suitable protocol for isolation of the RSV promotor and its use in construction of a plasmid vector is described in Gorman, et al., *Proc. Natl. Acad. Sci, USA,* 79:6777, (1982).

Other preferred plasmid vectors are pREP7 and pREV which are commercially available from Invitrogen of San Diego, Calif. For cloning of polynucleotides, a particularly suitable plasmid for production of mRNA is the pSP64T cloning vector described by Kreig, et al., *Nucleic Acids Res.*, 12:7057–7070, (1984). Any cDNA containing an initiation codon can be introduced into this plasmid and mRNA prepared from the expressed DNA templates using conventional techniques.

A particularly useful vector for administration of any SERCA2 polynucleotides according to the invention are those which contain a promoter that can be switched "on" or "off" after the vector has been administered to the patient.

Particularly efficacious examples of such promoters are the antibiotic inducible and ligand inducible nuclear receptor promoters. With respect to the latter, nuclear receptors represent a family of transcriptional enhancer factors that act by binding to specific DNA sequences found in target promoters known as response elements. Specific members of the nuclear receptor family include the primary intracellular targets for small lipid-soluble ligands, such as vitamin $D_3$ and retinoids, as well as steroid and thyroid hormones ("activating ligands"). Specific response elements in calcium transport regulatory proteins have been identified, including thyroid response elements (TRE's), CAM kinase and others, which are also present in the regulatory region of SERCA2 (see, FIG. 1). Such specific response elements may be used to control SERCA2 transcription in vivo as described below. In particular, SERCA2 gene expression is especially sensitive to thyroid hormone (Rohrer, et al., *J Biol. Chem.*, 266:8638–8646, 1991, the disclosure of which is incorporated herein for purposes of reference).

Nuclear receptors activated by specific activating ligands are well suited for use as promoters in eukaryotic expression vectors since expression of genes can be regulated simply by controlling the concentration of ligand available to the receptor. For example, glucocorticoid-inducible promoters such as that of the long terminal repeat of the mouse mammary tumor virus (MMTV) have been widely used in this regard because the glucocorticoid response elements are expressed in a wide variety of cell types. One expression system which exploits glucocorticoid response elements responsive to a wide variety of steroid hormones (e.g., dexamethasone and progesterone) is a pGRE2tk plasmid (containing one or more rat tyrosine amino transferase glucocorticoid response elements upstream of the herpes simplex virus thymidine kinase (tk) promoter in pBLCAT8+), transfected in HeLa cells (see, Mader and White, *Proc.Natl.Acad.Sci USA*, 90:5603–5607, 1993 [pGRE2tk]; and, Klein-Hitpass, et al., *Cell*, 46:1053–1061, 1986 [pBLCAT8+]; the disclosures of which are incorporated herein by this reference to illustrate knowledge in the art concerning construction of suitable promoters derived from nuclear receptor response elements ["NRRE promoters"]).

Another particularly suitable NRRE promoter for use in the invention is one which is inducible by the vitamin $D_3$ compound 1,25-dihydroxyvitamin $D_3$ and non-hypercalcemic analogs thereof (collectively, "vitamin $D_3$ activating ligands"). NRRE promoters inducible by vitamin $D_3$ activating ligands contain the vitamin $D_3$ receptor (VDR) response elements PurG(G/T)TCA which recognizes direct repeats separated by 3 base pairs. Vitamin $D_3$ response elements are found upstream of human osteocalcin and mouse osteopontin genes; transcription of these genes is activated on binding of the VDR (see, e.g., Morrison and Eisman, *J.Bone Miner.Res.*, 6:893–899, 1991; and, Ferrara, et al., *J.Biol.Chem.*, 269:2971–2981, 1994, the disclosures of which are incorporated herein by this reference to illustrate knowledge in the art of vitamin $D_3$ responsive inducible promoters). Recent experimental results from testing of a recombinant expression vector containing the mouse osteopontin VDR upstream of a truncated herpes simplex virus thymidine kinase (tk) promoter suggested that 9-cis-retinoic acid can augment the response of VDR to 1,25-hydroxyvitamin $D_3$ (see, Carlberg, et al., *Nature*, 361:657–660, 1993).

Ferrara, et al. also described vitamin $D_3$ inducible promoters in recombinant expression vectors constructed using multiple copies of a strong VDR; in particular, the mouse osteopontin VDR (composed of a direct repeat of PurGT-TCA motifs separated by 3 base pairs). This VDR conforms to the PurGG/TTCA consensus motifs which have previously been shown to be responsive not only to vitamin $D_3$, but also to thyroid hormone and/or retinoic acid. As many as three copies of the mouse VDR was inserted into pBLCAT8+; immediately upstream of the herpes simplex virus tk promoter. Transfection of the resulting VDREtk vector into COS cells (producing a "VDR expression system") proved to be particularly useful in that COS cells contain the nuclear retinoid X receptor (RXR) that has been shown to act as an auxiliary factor for binding of VDR to its response element. Conveniently, 1,25-dihydroxyvitamin $D_3$ and nonhypercalcemic analogs thereof have been approved for use in topical preparations by the United States Food and Drug Administration for the treatment of psoriasis and are commercially available.

In vivo tests of the NRRE promoters indicate that they are inducible on systemic exposure to their corresponding response elements (see, Tsou, et al., *Exp.Cell.Res.*, 214:27–34, 1994). Thus, use of an NRRE promoter recombinant expression vector for administration and expression of SERCA2 polynucleotides according to the invention permits control of expression to, for example, switch on expression when dosing is needed or switch off expression in the event of an adverse reaction to the expressed protein or peptide.

Another well-characterized "on/off" switch for use in a recombinant expression vector is the antibiotic (tetracycline) regulated promoter system. Means for construction of such a system are well-known in the art; for review in this regard, those of skill in the art may wish to consult Furth, et al., *Proc.Natl.Acad.Sci. USA*, 91:9302–9306, 1994 (tetracycline regulated control of gene expression in transgenic mice); Fishman, et al., *J.Clin.Invest.*, 93:1864–1868, 1993 (tetracycline control of cardiac gene expression); and, Niwa, et al., *Gene*, 108:193–200, 1991(use of the promoter system for high-expression transfectants). A SERCA2 encoding plasmid under the control of a tetracycline promoter system is described in Example 4 and shown in FIG. 2.

Various viral vectors that can be utilized in the invention include adenovirus, herpes virus, vaccinia, or an RNA virus such as a retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles.

This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, Ψ2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

Of the DNA expression vectors, adenovirus vectors are preferred for their efficiency of transfection (up to 70% in cardiac myocytes). Such vectors are also preferred for their ability to accept exogenous DNA of up to 7.5 kb in size as well as their susceptibility to production in high titers. Advantageously, adenovirus vectors survive intracoronary injection well (as compared to, for example, polylysine conjugates of SERCA2 polynucleotides).

The adenovirus is a double-stranded, linear DNA virus known to exist in at least 42 different serotypes. Serotype 5 is most commonly used as a recombinant expression vector, usually with the majority of the early phase E1a and E1b coding regions deleted to prevent replication (for a review in regard to the construction of replication deficient adenovirus vectors, those of skill in the art may wish to refer to Brody and Crystal., *Annals NY Acad.Sci.*, 716:90–101, 1994, the disclosure of which is incorporated herein for reference). A simian virus 40 (SV40) polyadenylation signal is typically used, with propagation in 293 cells (a transformed human embryonic kidney cell line). Such vectors can be produced in titers of up to 1012 plaque forming units/ml.

Figure 3:
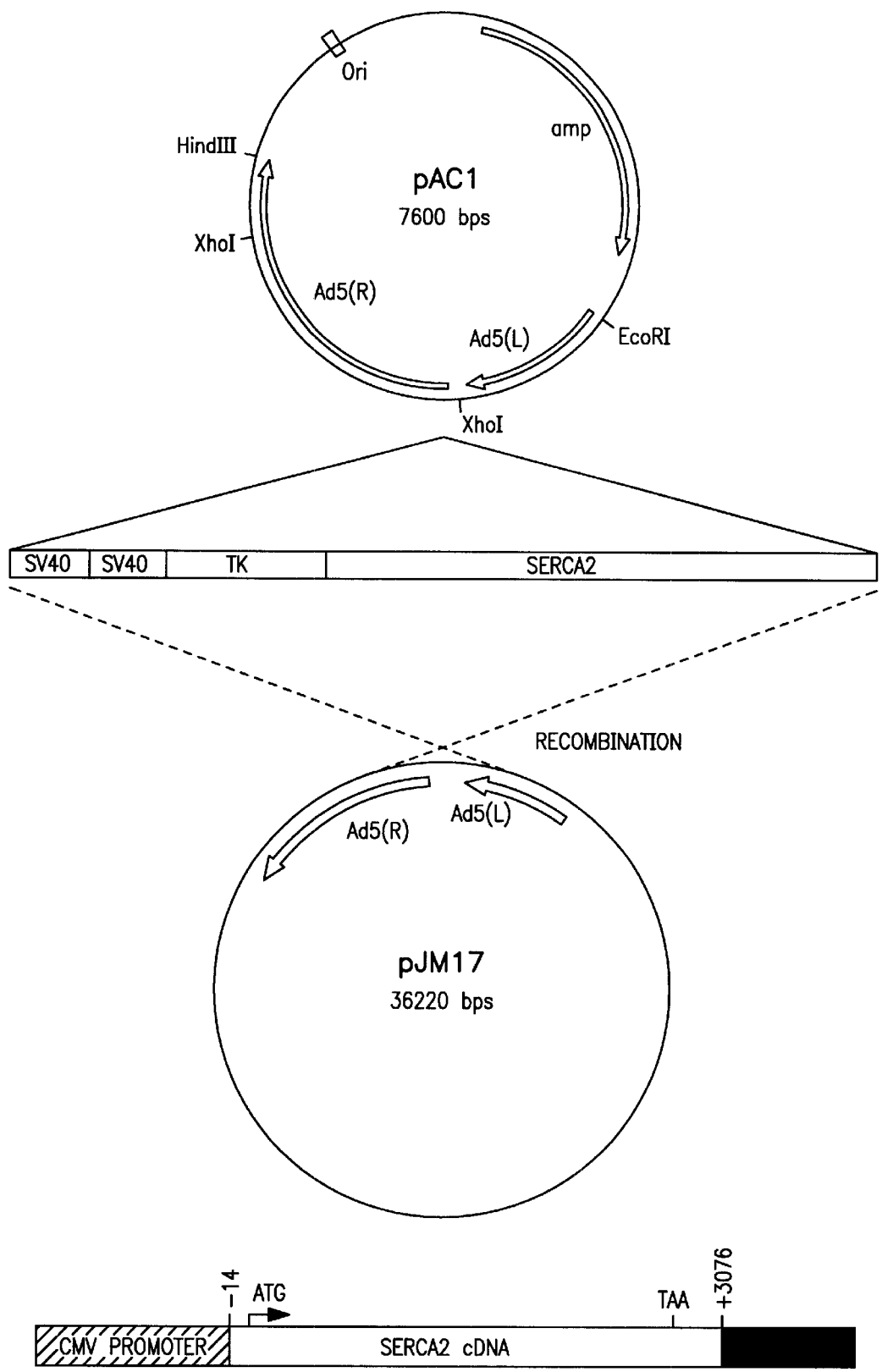
FIG. 3 is a map of a SERCA2 encoding adenovirus recombinant expression vector.

A particularly preferred adenovirus construct for use in the invention is shown in FIG. 3. As detailed further in Example 4, the construct is formed by cloning SERCA2 polynucleotide into a shuttle vector that contains a promoter, polylinker and partial flanking adenoviral sequences from which the E1a and E1b coding regions have been deleted. The resulting plasmid is then co-transfected (by conventional calcium/phosphate precipitation techniques) into 293 cells with plasmid JM17, a plasmid containing the entire human adenoviral 5 genome with an additional 4.3 kb insert (the construct product is too large to be encapsidated). Homologous rescue recombination results in adenoviral vectors which encode SERCA2 but propagate in 293 cells which have been transformed with E1a and E1b early phase proteins. Preferably, successful recombinants are plaque purified prior to propagation, then further purified by double CsCl gradient ultracentrifugation (see, Example 4) to maximally eliminate wild-type contamination.

The expected in vivo operability of the adenoviral construct shown in FIG. 3 is no longer than several months. However, with reconstitution of the function of the E3 coding region (which codes for proteins that provide the virus with protection against host immune surveillance), this life-span should be increased. Encapsulation of SERCA2 for liposomal delivery (as described in Section C below) should also limit immune destruction of the virus, as would use of a replicable adenovirus construct. However, given the risks which may be associated with integration of viral DNA into the host genome, use of such vectors would likely be limited to situations where long-term expression of the vector product was critical to the patient's survival.

By inserting one or more sequences of interest into the viral vector, along with another gene which encodes the ligand for a receptor on a specific target cell, for example, the vector can be rendered target specific. Retroviral vectors can be made target specific by inserting, for example, a polynucleotide encoding a sugar, a glycolipid, or a protein.

Preferably, avoidance of non-specific transfection of the recombinant expression vectors of the invention into myocardial cells other than target myocytes will be achieved through use of cardiac-specific promoters. Several such promoters are presently known and include avian β-actin (see, SERCA2 encoding plasmid map at FIG. 4 and Example 1). Those of skill in the art will know of, or can readily ascertain without undue experimentation, other specific polynucleotide sequences which can be inserted into the viral genome to allow target specific delivery of the viral vector containing the SERCA2 polynucleotides of interest.

C. PHARMACEUTICAL PREPARATIONS OF SERCA2 POLYNUCLEOTIDES

Compositions of SERCA2 polynucleotides and mixtures of SERCA2 polynucleotides may be placed into a pharmaceutically acceptable suspension, solution or emulsion.

Suitable mediums include saline and may, for those embodiments which do not rely on antigen presenting cells for delivery of the SERCA2 polynucleotides into target tissue, liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of SERCA2 polynucleotides may be lyophilized using means well known in the art, for subsequent reconstitution and use according to the invention.

In addition to the targeted vector delivery systems discussed supra, a colloidal dispersion system may also be used for targeted delivery. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of operatively encoding polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

It is expected that these techniques (and others which are conventionally used to facilitate drug delivery) may be adapted to preparation of SERCA2 polynucleotides for use in the methods of the invention by those of ordinary skill in the art without undue experimentation. In particular, although the approaches discussed in the preceding paragraphs have not, to the inventors' knowledge, been previously used for SERCA2 polynucleotide delivery to myocytes in vivo, it is believed that they are suitable for use to that end. For that reason, the references identified above, while not essential to the inventive methods, are incorporated herein by this reference. Specific examples illustrating this suitability are set forth infra.

D. METHOD FOR IN VIVO ENHANCEMENT OF CARDIAC SERCA2 ACTIVITY

For purposes of the invention, it is sufficient that the SERCA2 polynucleotides be supplied at a dosage sufficient to cause expression of the biologically active peptide encoded by the polynucleotide. Preferably, the level of expression achieved will be sufficient to substantially replace "normal" endogenous SERCA2 activity. Advantageously, the SERCA2 polynucleotides will be contained in a recombinant expression vector and formulated into a pharmaceutically acceptable composition (as described in Section C, supra).

"Normal" SERCA2 levels and activity will vary among individuals and cannot, therefore, be absolutely quantified for particular species. However, a desired SERCA2 expression level to achieve specific therapeutic ends (a "therapeutically beneficial amount") can be ascertained and maintained within acceptable clinical limits by monitoring pre- and post-treatment levels of SERCA2 protein as well as clinical signs of enhanced contractility and cardiac performance in a CHF heart. Means for monitoring SERCA2 levels are described infra at Section F.

Clinical signs of improvement in cardiac performance and accommodation of stresses associated with CHF are well-known to those of ordinary skill in the cardiological art and may be determined, for example, by monitoring blood flow, cardiac pumping volume and ventricular pressure (by, for example, angiography and echocardiography), calcium transport rates (by in vitro evaluation of cardiac fluid samples), tolerance studies (by, for example, monitoring heart rate in response to pressure overload stress on the heart) and general clinical signs of a lessening in CHF symptoms (for example, greater host endurance and easier respiration). Administered dosages may be modified to achieve particular therapeutic ends (e.g., overexpression of SERCA2 to boost calcium transport in hosts suffering from acute CHF conditions). Maximal and minimal ranges will also be defined by extrapolation of results from non-human animal data, such as from use of the models described above and larger mammalian species.

SERCA2 polynucleotide delivery will preferably be achieved by intravenous or intracoronary infusion (preferably using catheterization to minimize backflow of polynucleotide into the aortic root). Alternatively, to achieve greater, more immediate SERCA2 expression, the SERCA2 polynucleotides may be injected into the intraventricular wall (through, for example, a surgical thoracotomy technique) or introduced directly into a ventricle (by, for example, angiographic catheterization). SERCA2 expression will thereafter be monitored and the delivery repeated as necessary. Treated hosts should also be carefully monitored for adverse reactions, such as immune responses to the polynucleotides or SERCA2, as well as for excessive SERCA2 expression (as indicated by, for example, excessive prolongation of diastole).

In general, however, based on the results set forth in the Examples below, the risk of cytopathic or other adverse effects related to recombinant expression (adenovirus) delivery of SERCA2 polynucleotides to myocytes in vivo appears to be low and can be minimized with elimination of wild-type vector contaminants and other reduction in vector immunogenicity (such as by liposomal encapsulation of vectors).

E. ANIMAL MODELS FOR TESTING THE METHOD OF THE INVENTION

The rat has proven to be a reproducible experimental model of congestive heart failure which, despite the lack of collateral circulation in the rat heart, is acceptably predictive of human CHF conditions. In particular, rats which have undergone surgical ligation of the coronary artery are particularly good models of CHF after myocardial infarction in humans. The experimental protocols for the production and use of rats as CHF animal models have been well-described in the art; for reference, those of skill in the art may wish to refer to Pfieffer, et al., *Am.J.Med.*, 76:99–103, 1984; Johns and Olsen, *Ann.Surg.*, 140:675–682,1954; and, Selye, et al., *Angiology*, 11:398–407, 1960 (the disclosures of which are incorporated by this reference to illustrate knowledge in the art concerning the development and use of CHF animal models).

In addition, a transgenic animal model has been developed which is especially predictive of the impact on cardiac performance in CHF heart in which SERCA2 activity has been increased according to the method of the invention. A protocol useful in reproducing these transgenic animals (which express a SERCA2 transgene) is described below and is set forth in Example 1. The protocol generally follows conventional techniques for introduction of expressible transgenes into mammals. Those of ordinary skill in the art will be familiar with these applications and will be able to apply the techniques in the context of the present invention without undue experimentation.

For example, embryonal target cells at various developmental stages can be used to introduce transgenes. Different methods are used depending on the stage of development of the embryonal target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al., *Proc. Natl. Acad Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenisch, *Proc. Natl. Acad Sci USA* 73:1260–1264, 1976). Efficient infection of the blastomeres is obtained by enzymatic treatment to remove the zona pellucida (Hogan, et al., *Manipulating the Mouse Embryo*, Cold Spring Harbor Laboratory Press, Cold Spring Harbor, N.Y., 1986). The viral vector system used to introduce the transgene is typically a replication-defective retrovirus carrying the transgene (Jahner, et al., *Proc. Natl. Acad. Sci. USA*, 82:6927–6931, 1985; Van der Putten, et al., *Proc. Natl. Acad. Sci USA* 82:6148–6152). Transfection is easily and efficiently obtained by culturing the blastomeres on a monolayer of virus-producing cells (Van der Putten, supra; Steward, et al., *EMBO J.*, 6:383–388, 1987).

Alternatively, infection can be performed at a later stage. Virus or virus-producing cells can be injected into the blastocoele (Jahner, et al., *Nature*, 298:623–628, 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes, into the germ line, albeit with low efficiency, by intrauterine retroviral infection of the midgestation embryo (Jahner, et al., supra, 1982).

A third type of target cell for transgene introduction is the embryonal stem cell (ES). ES cells are obtained from pre-implantation embryos cultured in vitro and fused with embryos (Evans, et al., *Nature*, 292:154–156, 1981; Bradley, et al., *Nature*, 309:255–258, 1984; Gossler, et al., *Proc. Natl. Acad. Sci USA*, 83:9065–9069, 1986; and Robertson, et al., *Nature*, 322:445–448, 1986). Transgenes can be efficiently introduced into the ES cells by DNA transfection or by retrovirus-mediated transduction. These transformed ES cells can thereafter be combined with blastocysts from a non-human animal. The ES cells will thereafter colonize the embryo and contribute to the germ line of the resulting chimeric animal (see for review, Jaenisch, *Science*, 240:1468–1474, 1988).

Preferably, for use as an animal model in the context of the invention, the transgene of choice will be one which includes a promoter capable of leading to a relatively high expression level of SERCA2. A preferred promoter for use in this regard is the human CMV enhancer linked to a β-actin promoter (e.g., from an avian species) which includes a β-actin intron. For detection of transgene expression activity, a coding region for the Flag antigenic epitope described elsewhere above was included in the region of the transgene coding for the C-terminal region of SERCA2. As described in Example 1, transgene-expressing progeny of the founder animals live to adulthood; the transgene can be expected to be carried by at least about 15% of the progeny of a founder line.

F. METHODS FOR MONITORING IN VIVO EXPRESSION OF SERCA2

For purposes of monitoring expression of SERCA2, the SERCA2 polynucleotides to be introduced into a host according to the invention may be modified to include known reporter genes. For example, the pRSV lac-Z DNA vector described in Norton, et al., *Mol. Cell. Biol.*, 5:281, 1985, may produce β-galactosidase with protein expression. Luciferase and chloramphenicol acetyl transferase ("CAT"; see, e.g., Gorman, et al., supra, re construction of a pRSV-CAT plasmid) may also be used. Another useful reporter molecule is the Flag antigenic peptide, which can be readily detected by immunoassay. The 8 amino acid sequence for the Flag antigenic peptide and coding regions therefor are known in the art; for reference in this regard, those of skill in the art may wish to consult Chiang, et al., *Peptide Res.*, 6:62–64, 1993. Insertion of a reporter gene for coding at the C terminus of the SERCA2 protein (e.g., by insertion of the gene about 15 bp from the starting codon) will not interfere with the catalytic activity of SERCA2. Means for detection of the expression of such reporter genes are well-known in the art and will not be described in detail, but are summarized below.

For example, SERCA2 expressed in vivo after introduction of a SERCA2 polynucleotide according to the invention may be detected by immunoassays in which SERCA2 protein can be utilized in liquid phase or bound to a solid phase carrier. In addition, SERCA2 protein to be utilized in these assays can be detectably labeled in various ways. Further, antibodies to SERCA2 or a reporter gene product may be utilized to detect SERCA2 polynucleotide expression in assay samples, such as blood or serum.

Briefly, such antibodies may be produced by means which are well-known in the art. For example, antibodies which are specific for SERCA2 or reporter gene products may be produced by immunization of a non-human with antigenic SERCA2 or reporter gene peptides. Such peptides may be isolated from native sources (see, e.g., the method used to isolate rat SERCA2 reported in Popovich, et al., Am.J.Physiol., 261:E377–E381, 1991, the disclosure of which is incorporated herein for purposes of review) or may be synthesized without undue experimentation by commonly used methods such as t-BOC or FMOC protection of alpha-amino groups.

The latter methods involve stepwise synthesis whereby a single amino acid is added at each step starting from the C terminus of the peptide (see, Coligan, et al., *Current Protocols in Immunology,* Wiley Interscience, 991, Unit 9). Peptides for use in this regard can also be synthesized by various well known solid phase peptide synthesis methods, such as those described by Merrifield, J. Am. Chem. Soc., 85:2149, 1962, and Stewart and Young, *Solid Phase Peptides Synthesis,* (Freeman, San Francisco, 27–62, 1969), using a copoly(styrene-divinylbenzene) containing 0.1–1.0 mMol amines/g polymer.

On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation. The antigenicity of peptides of interest can be determined by conventional techniques to determine the magnitude of the antibody response of an animal which has been immunized with the peptide.

Once antigenic SERCA2 peptides are prepared, antibodies to the immunizing peptide are produced by introducing peptide into a mammal (such as a rabbit, mouse or rat). A multiple injection immunization protocol is preferred for use in immunizing animals with the antigenic peptides (see, e.g., Langone, et al., eds., "Production of Antisera with Small Doses of Immunogen: Multiple Intradermal Injections", *Methods of Enzymology* (Acad. Press, 1981). For example, a good antibody response can usually be obtained in rabbits by intradermal injection of 1 mg of antigenic peptide emulsified in Complete Freund's Adjuvant followed several weeks later by one or more boosts of the same antigen in Incomplete Freund's Adjuvant.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse or a rabbit). Because SERCA2 is presently believed to be fairly well conserved among mammalian species, use of a carrier protein to enhance the immunogenicity of SERCA2 proteins is preferred.

Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (see, for example, Coligan, et al., Unit 9, *Current Protocols in Immunology,* Wiley Interscience, 1991).

For their specificity and ease of production, monoclonal antibodies are preferred for use in detecting SERCA2 expression. For preparation of monoclonal antibodies, immunization of a mouse or rat is preferred. The term "antibody" as used in this invention is meant also to include intact molecules as well as fragments thereof, such as for example, Fab and F(ab')$_2$, which are capable of binding the epitopic determinant. Also, in this context, the term "mAb's of the invention" refers to monoclonal antibodies with specificity for SERCA2 or reporter gene products.

The general method used for production of hybridomas secreting monoclonal antibodies ("mAb's"), is well known (Kohler and Milstein, *Nature,* 256:495, 1975). Briefly, as described by Kohler and Milstein the technique comprised lymphocytes isolated from regional draining lymph nodes of five separate cancer patients with either melanoma, teratocarcinoma or cancer of the cervix, glioma or lung, were obtained from surgical specimens, pooled, and then fused with SHFP-1. Hybridomas were screened for production of antibody which bound to cancer cell lines.

Confirmation of antigen specificity among mAb's can be accomplished using relatively routine screening techniques (such as the enzyme-linked immunosorbent assay, or "ELISA") to determine the elementary reaction pattern of the mAb of interest. It is also possible to evaluate an mAb to determine whether it has the same specificity as a mAb of the invention without undue experimentation by determining whether the mAb being tested prevents a mAb of the invention from binding to the antigen of interest isolated as described above. If the mAb being tested competes with the mAb of the invention, as shown by a decrease in binding by the mAb of the invention, then it is likely that the two monoclonal antibodies bind to the same or a closely related epitope.

Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

SERCA2 monoclonal antibodies which recognize an epitope shared by MHCα and MHCβ will be particularly useful in determining that SERCA2 detected is essentially unaltered structurally. Such mAb's are described with sufficient detail to be reproduced by Dorn, et al., *Am.J.Physiol.,* 267:H400–H405, 1994, the disclosure of which is incorporated herein for use as a review and reference.

Examples of immunoassays which can be used to detect SERCA2 expression are competitive and non-competitive immunoassays in either a direct or indirect format. Examples of such immunoassays are the radioimmunoassay (RIA), the sandwich (immunometric assay) and the Western blot assay. Detection of antibodies which bind to SERCA2 or a reporter gene product can be done utilizing immunoassays which run in either the forward, reverse, or simultaneous modes, including immunohistochemical assays on physiological samples. Particularly preferred for use in this regard are the commercially available assay kits for detection of reporter gene products such as lac-Z or β-gal (e.g., β-galactosidase).

The concentration of antigen or antibody to used will vary depending on the type of immunoassay and nature of the detectable label which is used. However, regardless of the type of immunoassay which is used, the concentration of antigen or antibody to be utilized can be readily determined by one of ordinary skill in the art using routine experimentation.

Such antigen or antibodies can be bound to many different carriers and used to detect the presence of antibody or antigen specifically reactive thereto. Examples of well-known carriers include glass, polystyrene, polyvinyl chloride, polypropylene, polyethylene, polycarbonate, dextran, nylon, amylases, natural and modified celluloses, polyacrylamides, agaroses, and magnetite. The nature of the carrier can be either soluble or insoluble for purposes of the invention. Those skilled in the art will know of other suitable carriers for use in this regard, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Alternatively, SERCA2 polynucleotides may be detected (preferably in samples of target cells obtained through use of conventional cardiac tissue biopsy techniques) using quantitative polymerase chain reaction (PCR) protocols known in the art, general techniques for which are summarized below.

The nucleic acid from any histologic tissue specimen, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human DNA.

Where the target nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP which is known to denature DNA. The reaction conditions suitable for strand separation of nucleic acids with helicases are described by Kuhn Hoffmann-Berling (*CSH—Quantitative Biology*, 43:63, 1978) and techniques for using RecA are reviewed in C. Radding (*Ann. Rev. Genetics*, 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C.

The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by Southern blot analysis, without using radioactive probes. In such a process, for example, a small sample of DNA containing a very low level of target nucleotide sequence is amplified, and analyzed via a Southern blotting technique. The use of non-radioactive probes or labels is facilitated by the high level of the amplified signal.

A preferred method for performance of quantitative PCR is a competitive PCR technique performed using a competitor template containing an induced mutation of one or more base pairs which results in the competitor differing in sequence or size from the target gene template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions.

Once the aminated or biotinylated strands of the PCR products are immobilized, the unbound complementary strands are separated in an alkaline denaturing wash and removed from the reaction environment. Sequence-specific oligonucleotides ("SSO's") corresponding to the target and competitor nucleic acids are labelled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates.

This method is advantageous in that it is quantitative, does not depend upon the number of PCR cycles, and is not influenced by competition between the SSO probe and the complementary strand in the PCR product.

Alternatively, part of the polymerization step and all of the hybridization step can be performed on a solid phase support. In this method, it is an nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above.

A target to competitor nucleic acid ratio can be determined by detection of labelled oligonucleotide SSO probes using appropriate measurement means (preferably ELISA readers). The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

Molecules capable of providing different, detectible signals indicative of the formation of bound PCR products known to those skilled in the art (such as labelled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional non-competitive PCR protocol.

Those of ordinary skill in the art will know, or may readily ascertain, how to select suitable primers for use in the above methods. For further details regarding the above-described techniques, reference may be made to the disclosures in Kohsaka, et al., *Nuc.Acids Res.*, 21:3469–3472, 1993; Bunn, et al., U.S. Pat. No. 5,213,961; and to Innis, et al., *PCR Protocols: A Guide to Methods and Applications,* Acad.Press, 1990, the disclosures of which are incorporated herein solely for purposes of illustrating the state of the art regarding quantitative PCR protocols.

SERCA2 polynucleotides detected as described above can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Natl. Acad. Sci. USA,* 80:278, 1983), oligonucleotide ligation assays (OLAs) (Landegren, et al., *Science,* 241:1077, 1988), and the like. Molecular techniques for DNA analysis have been reviewed and are well known in the art (Landegren, et al., *Science,* 242:229–237, 1988).

The invention having been fully described, examples illustrating its practice are set forth below. These examples should not, however, be considered to limit the scope of the invention, which is defined by the appended claims.

In the examples, the abbreviation "min." refers to minutes, "hrs" and "h" refer to hours, and measurement units (such as "ml") are referred to by standard abbreviations.

EXAMPLE 1

Construction of SERCA2 Encoding Transgenes

Figure 4:
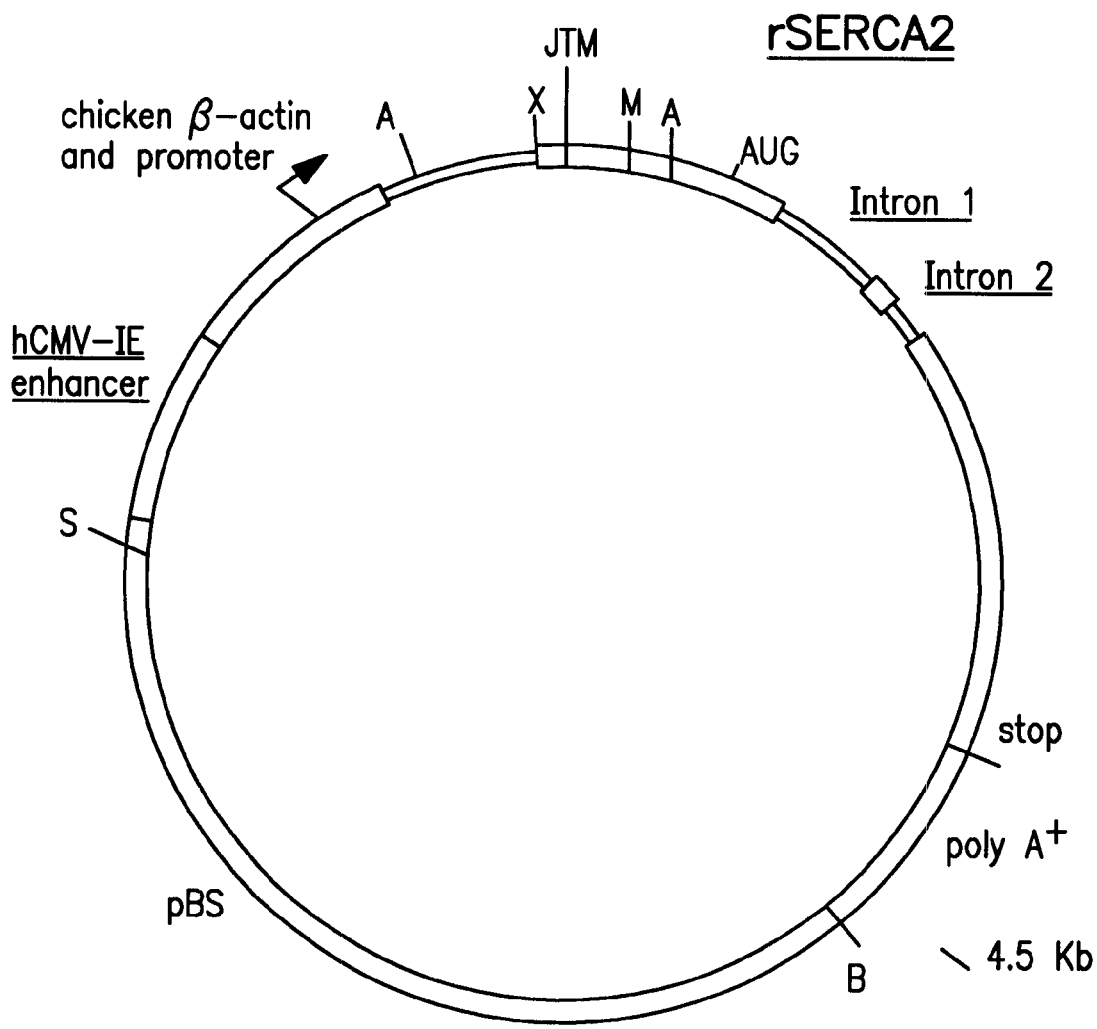
FIG. 4 is a map of a SERCA2 encoding plasmid under the control of a human CMV enhancer/β-actin chicken promoter system.

A map of an adenovirus construct under the control of the human cytomegalovirus (CMV) enhancer and β-actin chicken promoter which encodes SERCA2 is contained in FIG. 4. Briefly, the construct was made using a pCAGGS plasmid as a starting material (described in Niwa, et al., Gene, 108:193–200, 1993). The plasmid contains the CMV enhancer/β-actin promoter system.

Transcription in the pCAGGS plasmid starts at the first chicken β exon (200 bp long), followed by the first intron and 92 bp of the second chicken β exon. To this fragment, a modified genomic clone of rat SERCA2 polynucleotide (SEQ ID No: 1; modified by shortening the first exon by 218 bp to 398 bp followed by the initiation codon at position 500, followed by the first SERCA2 intron, second exon, second intron and part of third exon) was ligated to the 3'-end of the second exon of chicken β-actin. The remainder of the third SERCA2 exon and coding regions were linked in reading frame to the ligated third exon. The resulting construct therefore contains 1.8 kb of the CMV/β-actin promoter, 4.0 kb of SERCA2 coding sequence and 0.6 kb of intronic sequence. Through transfection of the vector into neonatal myocytes, the construct was confirmed to encode SERCA2 in a tissue (cardiac) specific manner.

For control of transgene expression, the construct is further modified to include a tetracycline (tet) operator (tetO) system. In that regard, a chimeric transactivator designated as the tetracycline controlled transactivator (tTA) which is constituted by the coding sequence for the tet binding domains of the bacterial tet repressor, fused to the transactivation domain of the herpes simplex virion protein 16 (VP16) can markedly stimulate transcription from minimal promoters containing tetO sequences. Due to the high affinity to ftTA and the fact that tet occupied tTA does not bind to tetO, tetracycline inhibits tTA depending transactivation. Thus, in animals having an expressible transgene under the control of the tetO system, exposure to tetracycline inhibits expression of the transgene (see, e.g., results reported in Chiang and Roeder, Peptide Res., 6:62–64. 1993). Tetracycline exposure at levels sufficient to regulate transgene activity does not lead to alterations in cardiac function.

To that end, a plasmid (e.g., p10–03) containing the tetO system will be used as a source of tetO (to be released by digestion). The tetO fragment is isolated on agarose gel and purified. The tetO fragment is then inserted 5' of the SERCA2 transgene in lieu of the CMV-β-actin promoter. A map of the resulting plasmid is contained in FIG. 2.

Animals which express the transgene for VP16 protein and animals which express the tetO/SERCA2 transgene are produced as described elsewhere above. The animals are then cross-bred to produce animals in which SERCA2 expression is regulable by exposure to tetracycline (e.g., from a fluid source containing tet hydrochloride of about 0.1 g/ml concentration). Using rats as the transgene recipients and by maintaining the founder line in Sprague-Dawley rats, transfer of the transgene can be expected to occur in at least 15% of the transgenic progeny.

As detailed below, expression of the SERCA2 transgene in the recipient animals and their progeny was confirmed by detecting SERCA2 mRNA and protein levels in histological and fluid specimens taken from animals which are positive for either the SERCA2 CMV/β-actin promoter transgene or the SERCA2 tetO transgene. In general, expression of either transgene peaks at 10–14 days after activation of transcription, then declines.

Figure 5:
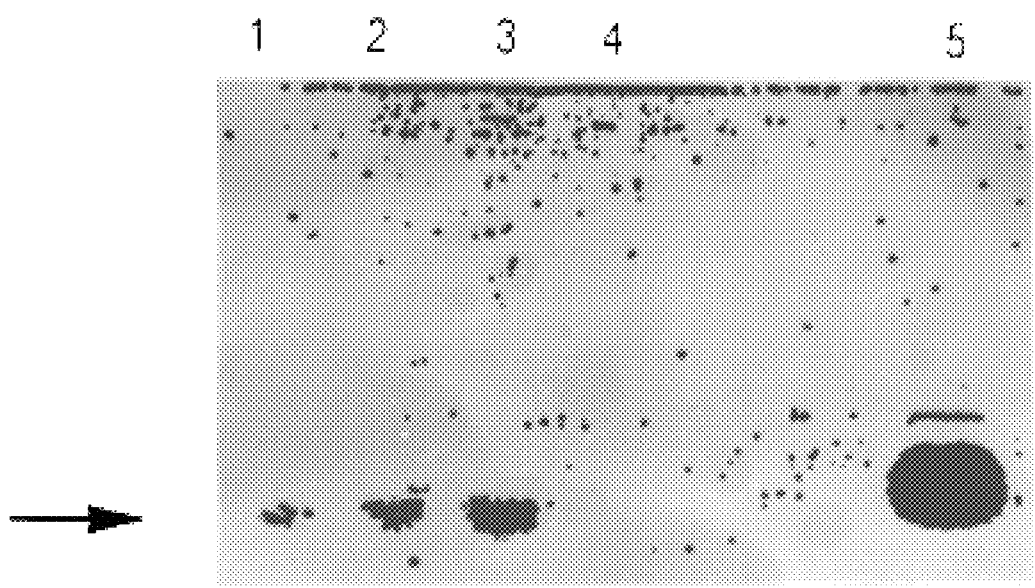
FIG. 5 is a Southern blot showing the presence of rat SERCA2 transgene DNA in mouse tissue samples. Lanes 1–3 represent different lines of transgenic founder mice; Lane 4 represents a transgene negative control mouse; and Lane 5 represents 1 ng of plasmid cut with Ap1.

Confirming the presence of transgene DNA in the transgenic animals, the results of a Southern blot analysis of genomic DNA from tissue cells removed from the tails of transgenic animals are shown in FIG. 5. The blot was probed with an 800 bp Ap1 fragment (comprised of 900 bp of chicken β-actin sequence and 300 bp of SERCA2 sequence) derived from the pCMV-β-actin plasmid (FIG. 4), Lanes 1–3 depict the results obtained from transgene positive founder animals showing the presence of SERCA2 polynucleotide; Lane 4 represents the results obtained from a control animal; and, Lane 5 depicts the results obtained from blotting of 1 ng of SERCA2 CMV/β-actin plasmid cut with Ap1.

Figure 6:
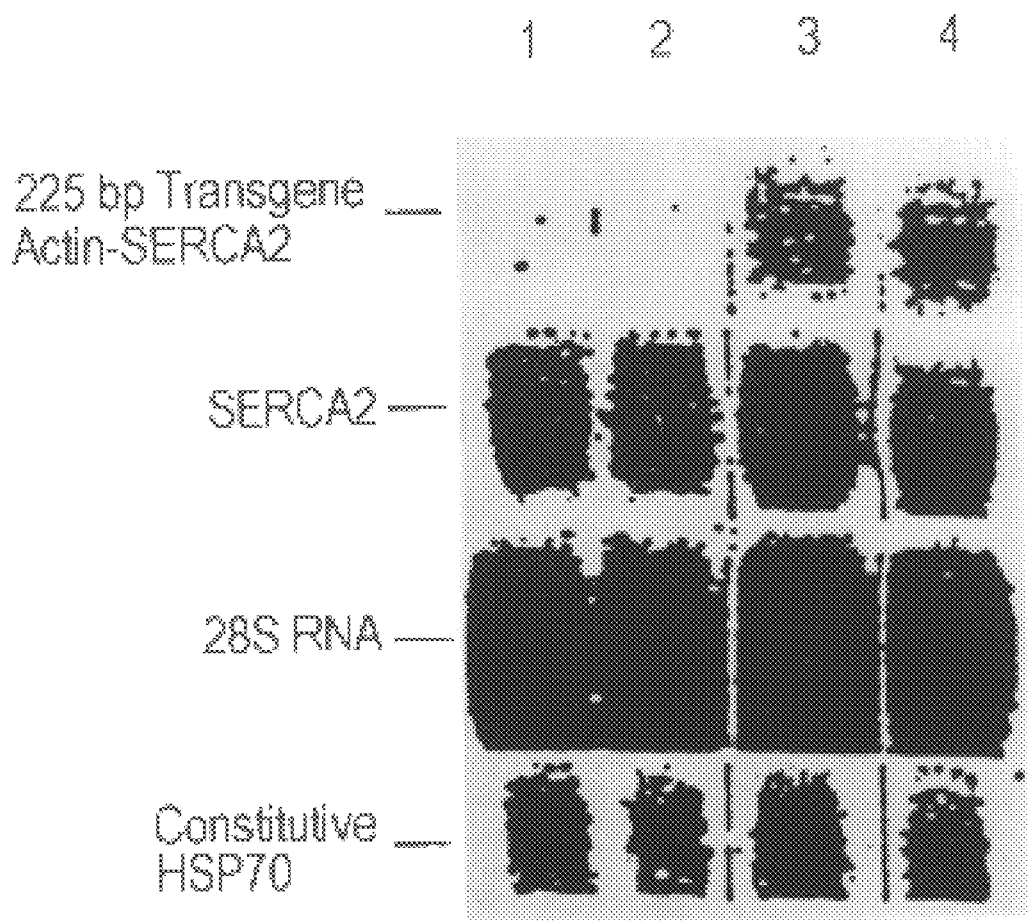
FIG. 6 is a Northern blot showing the presence of rat SERCA2 transgene mRNA in cardiac myocytes from mice. Lanes 1–2 represent transgene negative control mice; and, Lanes 3–4 represent transgene positive mice.

Confirming the presence of transgene RNA in the transgenic animals, the results of a Northern blot analysis of cardiac RNA obtained from SERCA2 transgenic and control animals are shown in FIG. 6. The blot was probed with fragments which span the junction in the plasmid of FIG. 4 between the β-actin coding region and SERCA2 coding region (comprising 100 bp of the former and 125 bp of the latter). Probes comprised of SERCA2 coding region, 28S RNA and cHSP (beat shock protein) 70 were also used. Lanes 1 and 2 depict results obtained from control animals, showing a signal for SERCA2 but not the transgene; Lanes 3 and 4 depict results obtained from the transgenic animals showing signals for both SERCA2 polynucleotide and the transgene. In the transgenic animals, SERCA2 transgene mRNA was detected at about 30% of the level of SERCA2 endogenous mRNA levels, which were equivalent to endogenous SERCA2 mRNA levels in control animals.

Figure 7:
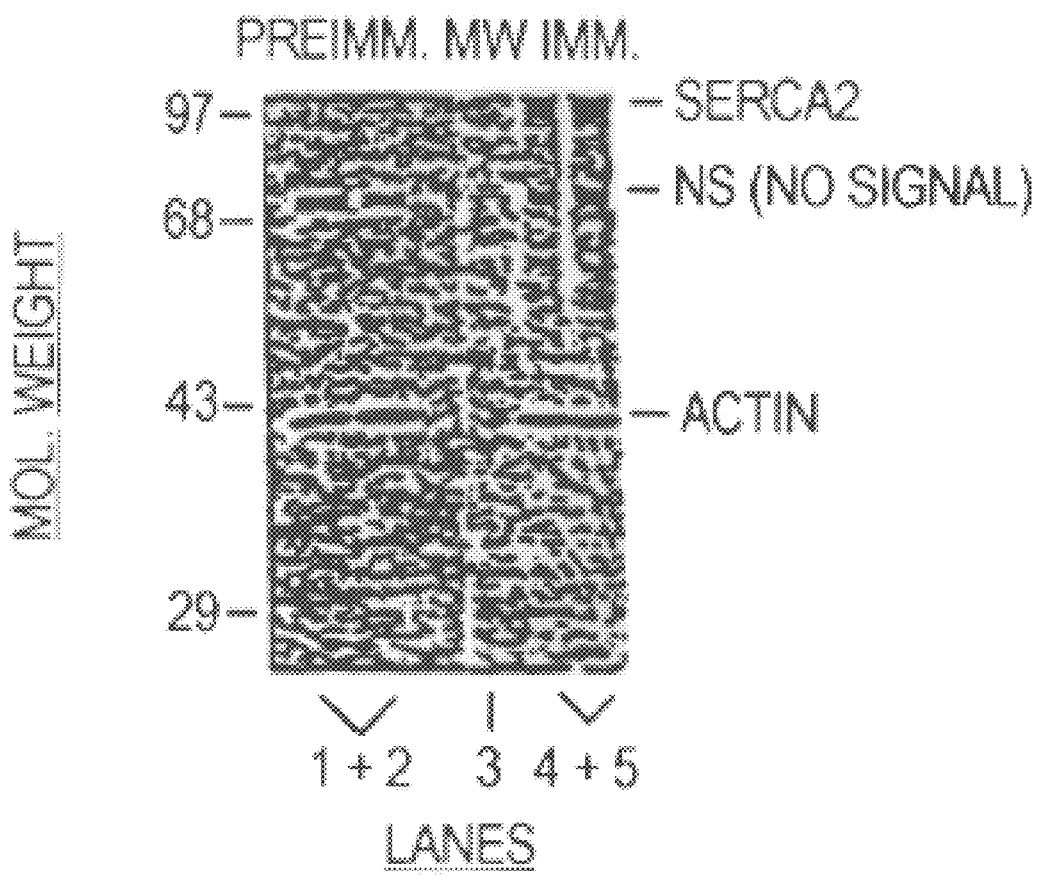
FIG. 7 is a Western blot showing SERCA2 transgene expression in mice. Lanes 1–2 represent α-sarcomeric actin expression; Lane 3 is a molecular weight marker; and, Lanes 4–6 represent SERCA2 expression.

Confirming SERCA2 protein expression by the transgene in the transgenic animals, the results of a Western blot analysis are shown in FIG. 7. The first two lanes illustrate bonding patterns observed when the blot was probed with preimmune serum from the animals and an anti-α-sarcomeric-actin mAb. The middle lane contains molecular weight markers; protein at about 110,000 in any other lanes represents SERCA2, with a non-specific band at 70,000 MW and an actin band at about 43,000 MW. The last two lanes show the pattern observed when the blots were probed with a mAb to rat SERCA2 at a 1:500 dilution. Thus, excess SERCA2 expression was obtained in the transgenic animals.

EXAMPLE 2

Pressure Overload and Cardiac Hypertrophy Models in SERCA2 Expressing Transgenic Animals and Control Animals To test the impact of additional SERCA2 expression in transgene positive animals under conditions which mimic those in CHF hearts, groups of sex, age and weight matched animals were treated to induce cardiac stenosis, to develop abdominal aortic constriction and to undergo salt loading. Under such conditions, such animals develop cardiac hypertrophy (CH) and cardiac abnormalities associated with pressure overload on the heart (PO), conditions which predominate in the CHF heart. For cardiac tissue specificity of transgene expression, the SERCA2 CMV/β-actin transgenic animals were used.

Briefly, to develop such animals, transgenic animals (rats of about 200–250 g body weight) developed as described in Example 1 and control animals are anesthetized for isolation of the abdominal aorta at the level of the celiac artery and, in the transgenic animals, for surgical constriction of the aorta above the renal artery using a stainless steel hemoclip (Edward Weck & Co., North Carolina). The latter procedure results in an reduction in aortic lumen size of about 50%.

About 2 days after surgery, the aortic constricted transgenic animals are injected twice a week intramuscularly with deoxycorticosterone suspended in sesame oil (25 mg/g body weight) and receive 1% sodium chloride in drinking water. All animals are monitored with cardiac ultrasound (echocardiography) for development of CH, which will generally occur within 1–2 weeks of surgery. In addition, the animals undergo an acute damage phase on imposition of pressure overload.

EXAMPLE 3

Adaptive Responses in Transgenic Animals to CHF Conditions

Transgenic animals tested at 6 weeks post-surgery underwent a significant decline in SERCA2 gene transcription (as determined by detecting mRNA levels for SERCA2), and typically begin to suffer heart failure at 10–12 weeks. SERCA2 mRNA and protein levels were determined by Northern and Western blotting as described above or by other assay techniques (e.g., PCR, also described above). Enzyme activity levels (as related to SR calcium transients) and left ventricular function in the transgenic and control animals were measured as described below. The same parameters for cardiac performance may be measured according to the protocols described below in other CHF animal models as well as in humans undergoing treatment according to the method of the invention.

Assessment of Cardiac Contractile Function

A. Protocol for Echocardiography to Determine Ventricular Functionality (In vivo)

Echocardiographic imaging is performed in a suitable animal model with a dual frequency phased array transducer operating at 7 Mhz and an ACCUSON™ 128 ultrasound console equipped with integrated doppler capability. Timing of echocardiographic events is correlated with simultaneous electrocardiographic recordings obtained from subcutaneous electrodes. Imaging depth is set at 2 cm and the sector angle at 60° which gives a frame rate of 50/sec. The power setting is 75 dB. 2D images may be used to select appropriate cursor positioning for M-mode recordings (which are acquired at 1000 lines/sec).

Lightly anesthetized animals are placed prone and imaging is performed through the left intercostal spaces near the sternum. Parasternal long and short axis views are acquired and recorded on videotape, and as stated above, 2D views are used to guide cursor placement for M-mode recordings which are performed at the mid-ventricular level. All relevant measurements are made from the 2D guided M-mode recordings using criteria to clinical conventions recommended by the American Society of Echocardiography. Septal wall thickness is measured from the leading edge to the trailing edge in end-diastole.

The posterior wall endocardium, identified as the line with the steepest systolic slope is measured from the leading edge of the posterior wall to the leading edge of the epicardial border in end-diastole. Left ventricular end-diastole dimension (LVEDD) is measured from the trailing edge of the intraventricular septum to the leading edge of the posterior wall at the point of maximum ventricular diameter. Lvend-systolic dimension (LVESD) is measured using the same criteria at the point of minimum ventricular diameter. Fractional shortening (FS) as an indication of systolic function is calculated as [(LVEDD-LVESD)/(LVEDD0)]100°.

B. Protocol for Micromanometer Catheterization to Draw Sample Fluid and to Determine Hemodynamic Parameters in the Heart (In vivo)

As illustrated in mice, adult mice (control and transgenic, with or without PO) weighing 20–30 g are anesthetized with a mixture of ketamine (100 mg/kg, IP) and xylazine (5 mg/kg, IP). Under a dissecting microscope animals are placed supine and a midline cervical incision is made to expose the trachea and carotid arteries. A blunt 20 gauge needle is then passed into the trachea to serve s the tracheal cannula which is connected to a volume cycled rodent ventilator (Harvard Apparatus) with a tital volume of 0.2 ml and respiratory rate of 100/min. Adequacy of ventilation is determined through visual inspection of chest expansion. After intubation, one carotid artery is cannulated with a fluid filled catheter (flame stretched PE to tubing) to measure aortic pressure. The chest is then opened and a 2F high fidelity micromanometer (Millar) is placed through the mitral valve and secured into LV.

Hemodynamic parameters are monitored while continuously measuring LV systolic and diastolic pressure, dP/dt max and min, and aortic pressure (using, for example, an on-line detection apparatus). Data is acquire at 1500 samples/sec and the frequency response of the high fidelity catheter is flat to over 10,000 Hz. These high sample rates are required for the accurate measurement of dP/dt in mice because of their rapid heart rate (ranging from 300–500/min).

Off-line analysis of hemodynamic parameters may include measurement of minimal and maximal LV and aortic pressure in addition to the calculation of the time constant of the LV pressure decay (tau). Determination of the tau value which reflects, especially the initial isovolumic phase of diastolic relaxation, is closely linked to SERCA2 function.

C. Protocol for Determination of Myocyte Shortening in Isolated Muscle Biopsy Tissue (In vitro)

As the protocol is illustrated in rats, left ventricular papillary muscle is excised, avoiding passive stretching, in oxygenated Tyrode's solution containing 25 mM BDM to minimize cutting injury and prevent contracture. The ends are attached by tying short lengths of 5–0 silk suture to the ventricular wall and valve ends of the preparation avoiding over-stretching. One end of the muscle will be attached to the glass rod of a Cambridge 400 Isometric force transducer (5 g full scale, 100 $\mu$g resolution) and the other end attached to a small stainless steel hook on a translation stage (Newport 423, ±1 $\mu$m) for muscle length control. For convenient viewing, the 1 ml test bath will be in the field of view of an Olympus SZ45 stereo microscope. The temperature is maintained in the bath at 33° C.

The muscle will then be adjusted to slack length at which resting force first registers on the transducer channel, the BDM will be washed out and bipolar stimulating electrodes lowered into the bath (using, for example, a Gras stimulator apparatus). Muscles will be stimulated at 0.2 Hz (20% above threshold), and after 30 minutes, the superfusate will be switched from 0.5 to 2.0 mM [$Ca^{2+}$]. All perfusates will be bubbled with 100% $O_2$.

Steady state isometric tension development will be measured at increments of muscle length and expressed as fractions of $L_{max}$ at which the developed tension becomes maximal. To correct for the short length of muscle sample used (in extrapolating results to muscle tissue performance in vivo), the shortening strain at the time of peak tension is measured using pairs of surface microspheres placed on the muscle and recorded with a video camera.

The marker positions are preferably detected and digitized using NIH Image 1.47 on a Macintosh Centris 650 with a Data Translation video frame grabber board. Correcting the length scale by using strain with respect to any fixed reference length has been shown to eliminate the descending limb of the length-tension curve.

Contractility is expressed as the slope of the isometric stress-strain relation, in which the stress is computed from the developed tension (total resting) divided by the cross-sectional area of the muscle. The cross-sectional area is estimated after the mechanical tests by dividing the volume of the specimen (determined from its weight) by the length of the unloaded muscle between the ends. Repeating these protocols as a function of extracellular $Ca^{2+}$ concentration between 0.5 and 2.5 mM will enable the underlying $Ca^{2+}$ sensitivity of these preparations to be characterized.

To characterize SERCA2 function and EC coupling in these experiments further, SECRA2 pump function is studied by measuring relaxation time when Na/Ca exchange is blocked with Na-free Tyrode's and when sarcoplasmic reticulum calcium accumulation is blocked by 10 mM caffeine. When Na/Ca exchange is clocked, relaxation time is slowed by about 30%. Relaxation properties of the test muscles will be determined as functions of muscle length and calcium from tracings of the isometric tension recorded on the chart recorder (e.g., the Gould 2200 recorder) and microcomputer acquisition system (commercially available from, for example, Strawberry Tree) at high speed (40 mm/sec). Measured parameters will include the time from peak tension to 90% recovery and the exponential time constant of isometric force decay. These measurements will also be subject to, and are correctable for, the artifact described above, since studies have shown that isometric relaxation is significantly prolonged when muscle length is controlled to keep sarcomere length in the undamaged central muscle constant.

Using the same approach described above, contractile studies can also be performed using long, thin, and uniform trabeculae isolated under a dissecting microscope from the left ventricle of rats. Studies using trabeculae will provide more specific information on absolute alterations in diastolic contractile mechanics independent of artifacts due to series of elastance of the muscle not available from conventional papillary muscle preparations. Other regions of the left ventricular wall can be used to isolate cardiac myocytes for edge detection and intracellular $Ca^{2+}$ transient studies.

D. Protocol for Isolation of Cardiac Myocytes and Evaluation of Calcium Transients Levels (In vitro)

Cardiac myocytes may be prepared from adult rat hearts using a collagenase perfusion method. The myocytes can be maintained in the absence or presence of 4% fetal calf serum for at least 4 days and maintain morphological and metabolic characteristics of adult cardiac myocytes. From the heart of one adult rat, $9-10 \times 10^6$ viable myocytes can be obtained.

Cardiac myocytes can also be prepared from pieces of the ventricular wall. This will allow to determine myocyte function, papillary muscle function and parameters related to SERCA2 gene expression and SERCA2 function obtained from the same heart. To this end, the ventricular tissue is minced and washed in $Ca^{2+}$-free modified Joklik minimum essential medium (MEM) supplemented with 25 mM $NaHCO_3$; 3.4 mM $MgCl_2$; 30 mM taurine, and 2 mM camitine. The tissue is then digested with MEM containing 0.1% collagenase type II (Worthington); 0.1% BSA fraction V, and 25 $\mu$M $CaCl_2$. Enzymatic digestion is continued for 30–40 minutes while gently stirring the tissue at 32° C. under continuous oxygenation. Complete dispersion of the cells is finally achieved by gentle trituration with a wide bore serological pipette.

The cells are then filtered through 300 $\mu$M nylon mesh and washed. Calcium levels are then gradually increased to a field concentration of 1 $\mu$M. This procedure can yield up to $2 \times 106$ cells/heart of which 60–70% are rod shaped viable myocytes usable in the studies described below.

Isolated adult rat cardiac myocytes (non-plated) are suspended in 10 ml of a solution containing 118 m NaCl; 4.8 mM KCL; 1.2 mM $NaH_2PO_4$; 1.2 mM mg $SO_4$; 1 mM $CaCl_2$; 11 mM glucose and 25 mM Na-N-2-hycroxyethylpiperazine-N-2-ethanesulfonic acid, 500 $\mu$l of the cell suspension is added to 1.5 ml of normal Tyrode solution and 5 $\mu$l of a 1 mM solution of the acetoxymethyl ester derivative of Indo I in DMSO is added. Cells are incubated at room temperature for 15–20 minutes. Cells are then selected for study based on uniformity of indo I loading and rod-shaped cell morphology with good striations. Cells are transferred to a small perfusion chamber mounted on the stage of a Nikon Diaphot microscope equipped with quartz optics. Cells are allowed to settle to the bottom of the perfusion chamber and are perfused continuously at 5 ml/min with Tyrode solution gassed with 90% $O_2$-5% $CO_2$ and kept at 37° C. Cells are driven at 0.2, 0.33, 1.0, 2.0 and 5.0 Hz with an external platinum electrode and $Ca^{2+}$ transients are measured fluorometrically. Similar studies can also be performed using neonatal rat or mouse myocytes. Infection of neonatal myocytes with Adv SERCA2 (FIG. 3) markedly decreases the calcium transient.

Figure 9:
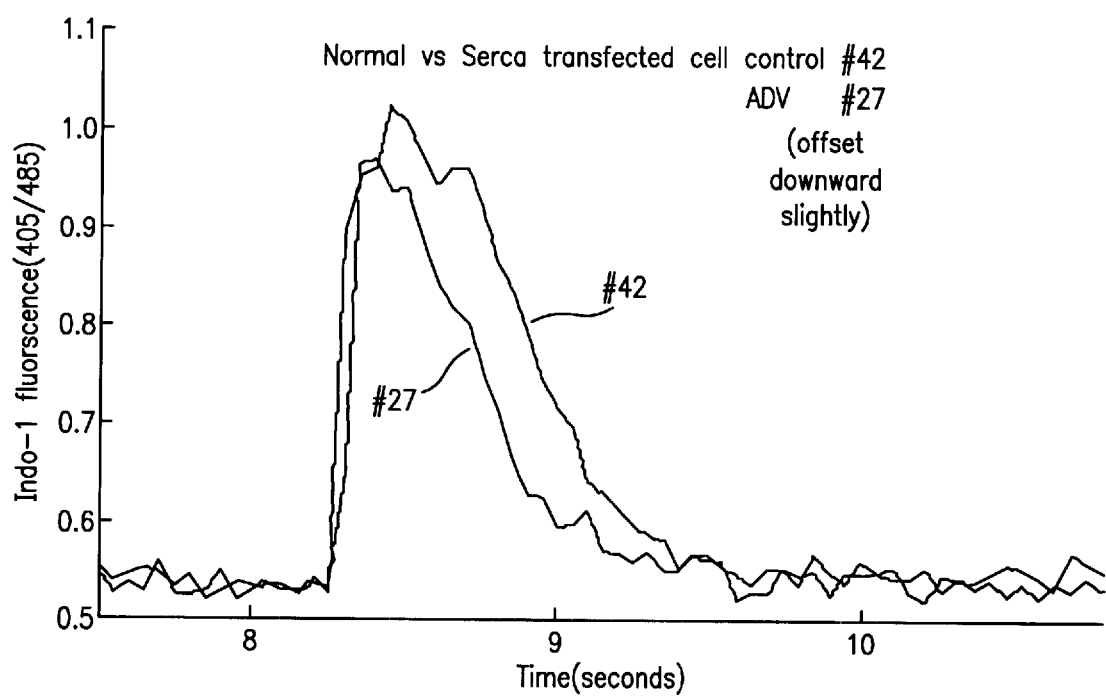
FIG. 9 depicts detected calcium transients in a neonatal myocytes transfected with the adenovirus vector of FIG. 3

With respect to calcium transients levels, the time to have maximal decrease in $calcium^{2++}$ transients was significantly shortened in SERCA2 transgene positive myocytes to a degree similar to that observed in vitro (Example 5; FIG. 9; p0.05). With respect to ventricular pressures, the maximal pressure achieved in the left ventricle (LVdP/dt max) was significantly greater in the transgenic animals, while at minimal levels, the ventricular muscles showed a trend toward faster diastolic relaxation in transgenic animals (n=3; as compared to controls where n=5). SERCA2 mRNA and protein levels detected in the animals are described in Example 1 and shown in FIGS. 6 and 7. These data prove the principle that calcium transport and diastolic relaxation of heart muscle is beneficially affected by application of the method of the invention in a predictive animal model.

EXAMPLE 4

Construction of a SERCA2 Expressing Adenovirus Vector

The construct was formed by cloning SERCA2 polynucleotide (FIG. 1) into a shuttle vector that contains a promoter, polylinker and partial flanking adenoviral sequences from which the E1a and E1b coding regions have been deleted. The resulting plasmid was then co-transfected (by conventional calcium/phosphate precipitation techniques) into 293 cells with plasmid JM17, a plasmid containing the entire human adenoviral 5 genome with an additional 4.3 kb insert (the construct product is too large to be encapsidated; see, FIG. 3 [vector map]). Homologous rescue recombination results in adenoviral vectors which encode SERCA2 but propagate in 293 cells which have been transformed with E1a and E1b early phase proteins.

More specifically, a replication deficient adenovirus vector was constructed as described in Graham, *EMBO J*, 3:2917–2922,1984 (the disclosure of which is incorporated herein for purposes of illustrating knowledge in the art concerning construction of such vectors). The vector has an insertion limit of about 5 kb. The transgene is cloned into an XbaI site of a shuttle plasmid pACI, which contains 5' adenovirus sequences flanking an XbaI site. In this instance, the transgene included SV40 enhancers, a SERCA2 encoding minigene and either a TK promoter or a CMV promoter, the latter of which is preferred. Each SV40 enhancer contains 70 bp. A useful CMV promoter containing plasmid source is pACCMVpLPA, wherein 670 bp of the CMV promoter including sequences past the transcription start is followed by a multiple cloning site which markedly eases the cloning approach (see, for a description of the pACCMVpLPA plasmid, McPhaul, et al., *J.Biol.Chem.*, 268:26063–26066, 1993). In either case, the transcription start will be in the promoter, the total size of which varies with the promoter used.

The promoter was fused by blunt-ended ligation to the rat SERCA2 cDNA clone. The SERCA2 clone contains the entire coding sequence including the stop and polyadenylation signals. The transcribed non-translated first exon of the SERCA2 gene was shortened by the first 232 bp. The 5' end of the SERCA2 mRNA corresponding to the first exon therefore contains 268 bp 5' from the translation start instead of the full-length first exon. A fragment corresponding to the full length exon would contain 500 bp 5' from the translational start. The SERCA2 transgene used is therefore 181 bp shorter than the SERCA2 mRNA transcribed from the genomic clone.

Figure 8:
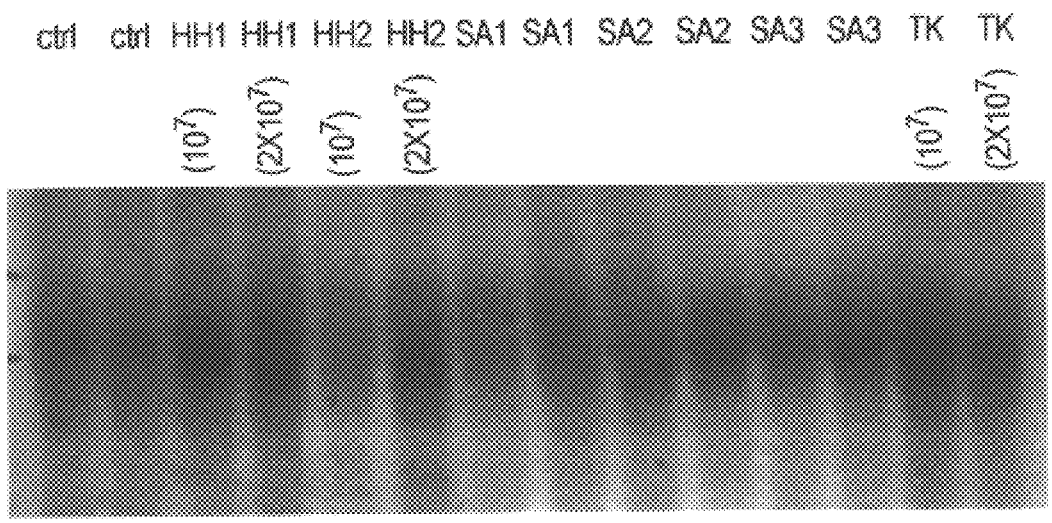
FIG. 8 is a Northern blot showing the presence of rat SERCA2 mRNA in cardiac myocytes from mice transfected with one of several SERCA2 encoding adenoviruses; i.e., vectors under the control of a CMV promoter (HH-1, HH-2 and SAI-3) or the TK promoter (TK). A control construct did not contain a SERCA2 polynucleotide (ctrl). Numbers in brackets indicate the number of plaque-forming units (pfu) of each construct and were determined by infecting L6 cells with adenovirus constructs for 48 hours, extracting and resolving total cellular RNA on gels, then hybridizing a SERCA2 CDNA to the RNA in Northern analysis.

Transfected cells were monitored for evidence of cytopathic effect for 10–14 days after transfection. To identify successful recombinants, cell supernatant from plates showing a cytopathic effect was treated with proteinase K (50 mg/ml with 0.5% sodium dodecyl sulfate and 20 mM EDTA) at 56° C. for 60 min., then phenol/chloroform extracted and ethanol precipitated. Successful recombinants were identified with PCR using primers complementary to the CMV promoter and SV40 polyadenylation sequences or to the TK promoter to amplify the insert. Primers were also designed to concomitantly amplify adenoviral sequences. The presence of SERCA2 mRNA in the transfectants was confirmed by Northern analysis as shown in FIG. 8; "HH-1","HH-2" and "SA1–SA3" are the CMV/SV40 constructs while "TK" is the TK promoter construct and "ctrl" indicates a control construct without SERCA2 polynucleotide.

Successful recombinants then underwent two rounds of plaque purification. Viral stocks were propagated in 293 cells to titers ranging between 1010 and 1012 viral particles, then were purified by double CsCl gradient centrifugation prior to use. Cells were infected at 80% confluence and harvested at 36–48 hours. After freeze-thaw cycles, the cellular debris was pelleted by standard centrifugation and the virus further purified by double CsCl gradient ultracentrifugation (discontinuous 1.33/.145 CsCl gradient; cesium prepared in 5 mM Tris, 1 mM EDTA(pH7.8) at 90,000×g for 2 hrs., then 105,000×g for 18 hrs.

Prior to in vivo use, the viral stocks were desalted by gel filtration through SEPHAROSE™ columns (i.e., G25 SEPHADEX™). The resulting viral stock had a final viral titer in the $10^{10}$ to the $10^{12}$ viral particles range. The adenoviral construct was highly purified; i.e., with no detectable, replicative (wild-type) particle contamination.

EXAMPLE 5

In Vitro Evaluation of Cardiac Myocyte Function After Transfection with a SERCA2 Expressing Adenovirus Vector Intracellular calcium transients were measured in cardiac myocytes isolated as described in Example 3 and transfected with adenoviral vector constructs made as described in Example 4. Briefly, neonatal cardiac myocytes were transfected with the SERCA2 adenoviral vector and calcium transients measured as described in Example 3 and compared to control (untransfected) cells. In FIG. 9, cell #42 is representative of the average behavior of control neonatal cardiac myocytes, while cell #27 is representative of the average behavior of transfected neonatal cardiac myocytes (ADV). As shown in FIG. 9, the time to half maximal decrease in the calcium transients was shortened by 33±19% (n=4; p≦0.01) in transfected cells in comparison to control cells. These data provide proof of the principle that calcium transients is enhanced in SERCA2 ADV transfected myocytes, a result which, if measured in vivo, would encourage more rapid diastolic relaxation in heart muscle (see, Example 3).

EXAMPLE 6

In vivo SERCA2 /ADV Transfection of Cardiac Myocytes in Pig Myocardium and Immune Responses Thereto The SERCA2 /ADV vector described in Example 4 was modified to include a gene to operatively encode β-galactosidase as a reporter molecule. An anesthetized, ventilated 40 kg pig underwent thoracotomy and isolation of the left circumflex and left anterior descending coronary arteries. A 26 gauge butterfly needle was inserted into the mid-left anterior descending (LAD) coronary artery and the vector ($1.5 \times 10^5$ viral particles) was injected in a 2 ml. volume. The animal's chest was then closed and the animal permitted to recover from the procedure.

Four days after surgery, the animal was sacrificed by humane means. The heart was removed and fixed with perfused glutaraldehyde, sectioned and incubated with X-gal for 16.5 hrs. After imbedding and sectioning, the tissue was counterstained with eosin.

Microscopic analysis of tissue sections (transmural section of LAD bed 72 hrs after intracoronary injection of vector) confirmed that 50–60% of the cells stained positively for presence of the β-gal reporter molecule. The negative control was derived from areas of myocardium remote from the injection site, where β-gal staining was not observed. In this study, as well as subsequent repetitions of the study showing gene expression after 14 days (n=5), no evidence of inflammation or necrosis was observed at the sites of transfection.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

What is claimed is:

1. A method for augmenting SERCA2 mediated calcium ion transport into the sarcoplasmic reticulum of cardiac myocytes of a host, the method comprising delivering an adenoviral recombinant expression vector containing a SERCA2 encoding transgene into host cardiac muscle, wherein expression of the transgene induces an augmentation in SERCA2 mediated calcium ion transport in treated myocytes, as compared to untreated myocytes.

2. The method according to claim 1 wherein the adenoviral recombinant expression vector is contained in a colloidal dispersion system.

3. The method according to claim 1 wherein the host has been diagnosed as suffering from congestive heart failure.

4. The method according to claim 3 wherein the host is a human.

* * * * *